(12) United States Patent
Chagnon et al.

(10) Patent No.: US 12,128,221 B2
(45) Date of Patent: Oct. 29, 2024

(54) DYNAMIC MIXING AND DELIVERY SYSTEM FOR MIXING A THERAPEUTIC AGENT IN AN INJECTOR OR AUTOINJECTOR

(71) Applicant: Windgap Medical, Inc., Watertown, MA (US)

(72) Inventors: Jeffrey Thomas Chagnon, Watertown, MA (US); Adam R Standley, Brookline, MA (US); Zachery John Dusterhoft, Waltham, MA (US); Brent A Buchine, Austin, TX (US)

(73) Assignee: Windgap Medical, Inc., Watertown, MA (US)

( * ) Notice: Subject to any disclaimer, the term of this patent is extended or adjusted under 35 U.S.C. 154(b) by 226 days.

(21) Appl. No.: 17/336,263

(22) Filed: Jun. 1, 2021

(65) Prior Publication Data
US 2022/0001112 A1    Jan. 6, 2022

Related U.S. Application Data

(60) Provisional application No. 63/032,311, filed on May 29, 2020.

(51) Int. Cl.
*A61M 5/315* (2006.01)
*A61M 5/19* (2006.01)
(Continued)

(52) U.S. Cl.
CPC .......... *A61M 5/31596* (2013.01); *A61M 5/19* (2013.01); *A61M 5/2066* (2013.01);
(Continued)

(58) Field of Classification Search
CPC .. A61M 5/31596; A61M 5/19; A61M 5/2066; A61M 5/3202; A61M 5/3294;
(Continued)

(56) References Cited

U.S. PATENT DOCUMENTS 3,451,393 A    6/1969   Sarnoff
4,689,042 A *  8/1987   Sarnoff .............. A61M 5/2066
                                                  604/191

(Continued)

FOREIGN PATENT DOCUMENTS

JP    2015-144676 A    8/2015
WO   WO-86/001120 A1   2/1986

(Continued)

OTHER PUBLICATIONS

International Search Report and Written Opinion for International Application No. PCT/US21/35318 dated Nov. 21, 2021, 15 pages.

(Continued)

*Primary Examiner* — Brandy S Lee
*Assistant Examiner* — Fatimata Sahra Diop
(74) *Attorney, Agent, or Firm* — Stephen J. Kenny; Foley Hoag LLP

(57) ABSTRACT

A mixing device configured to hold two containers, each having a separate medicament component disposed therein. A fluidic channel is provided that upon creating fluidic communication with each container once seals about each container are opened. Then a transfer mechanism can transfer the medicament components from one container to the other container until ready to be delivered or transferred through the fluidic channel through a delivery assembly.

21 Claims, 41 Drawing Sheets

(51) Int. Cl.
   *A61M 5/20* (2006.01)
   *A61M 5/32* (2006.01)
(52) U.S. Cl.
   CPC ........ *A61M 5/3202* (2013.01); *A61M 5/3294* (2013.01); *A61M 2005/202* (2013.01); *A61M 2005/2073* (2013.01); *A61M 2005/31598* (2013.01)
(58) Field of Classification Search
   CPC .... A61M 2005/202; A61M 2005/2073; A61M 2005/31598; A61M 5/2033; A61M 2005/2451; A61M 2005/247; A61M 2005/3247; A61M 2005/3267; A61M 5/31501; A61M 5/502; A61J 1/2093; A61J 1/22
   See application file for complete search history.

(56) References Cited

U.S. PATENT DOCUMENTS

| | | |
|---|---|---|
| 6,387,074 B1 | 5/2002 | Horppu et al. |
| 9,731,073 B2 * | 8/2017 | Laugere ................. A61M 5/19 |
| 9,889,260 B2 | 2/2018 | Laugere et al. |
| 10,195,344 B2 | 2/2019 | Ferriter et al. |
| 2010/0318063 A1 * | 12/2010 | Soll ........................ A61M 5/19 604/82 |
| 2013/0245604 A1 | 9/2013 | Kouyoumjian et al. |
| 2016/0279323 A1 | 9/2016 | Willoughby et al. |
| 2019/0240407 A1 | 8/2019 | Constantineau et al. |
| 2021/0205538 A1 * | 7/2021 | Egloff ................ A61M 5/31511 |
| 2022/0001112 A1 | 1/2022 | Chagnon et al. |

FOREIGN PATENT DOCUMENTS

| | | | |
|---|---|---|---|
| WO | WO-86/06967 A1 | 12/1986 | |
| WO | WO-2008051925 A2 * | 5/2008 | .............. A61M 5/19 |
| WO | WO-2013/171311 A1 | 11/2013 | |
| WO | WO-2018/001790 A1 | 1/2018 | |

OTHER PUBLICATIONS

Supplementary European Search Report for EP Application No. 21811959.2 dated Dec. 12, 2023, 8 pages.

* cited by examiner

100

100

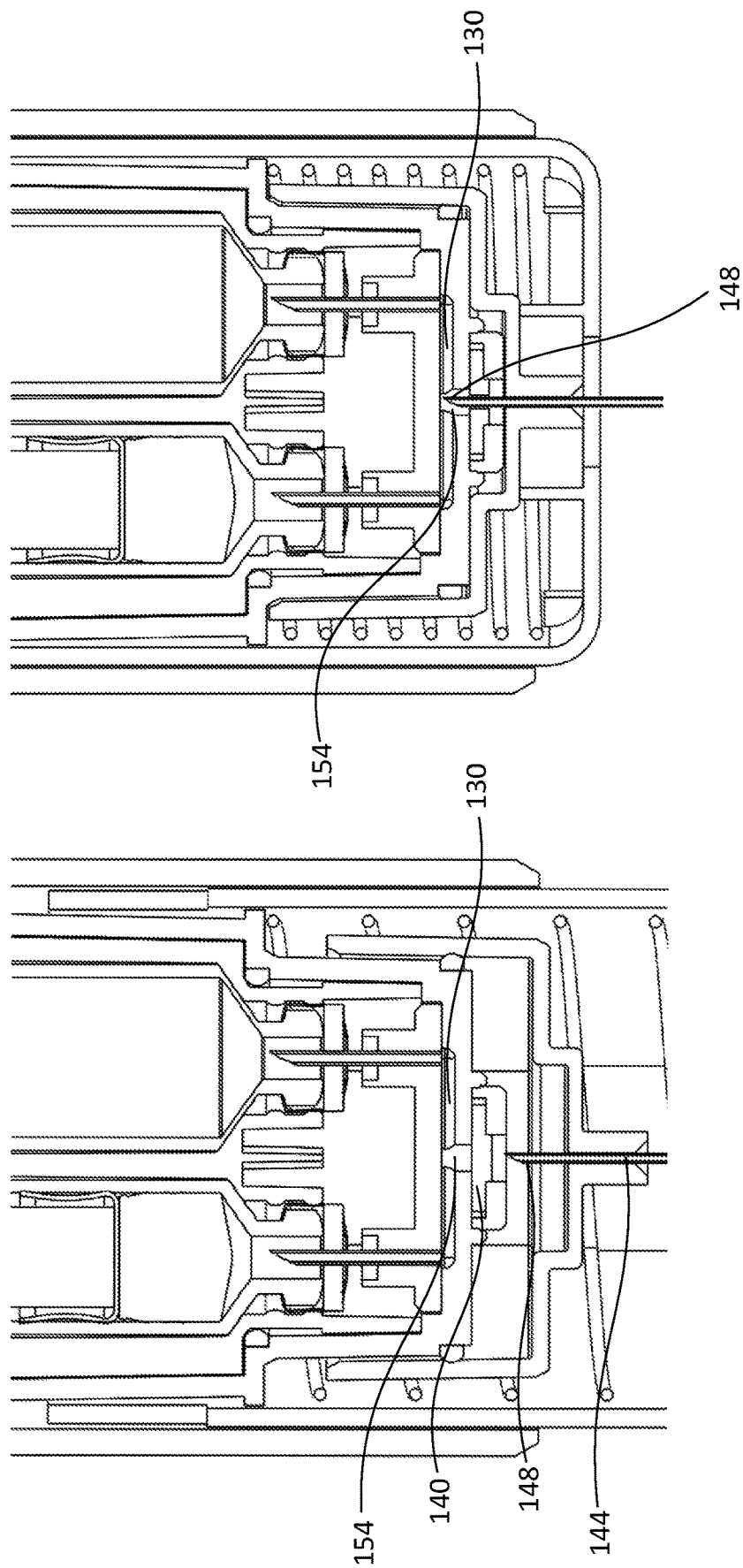

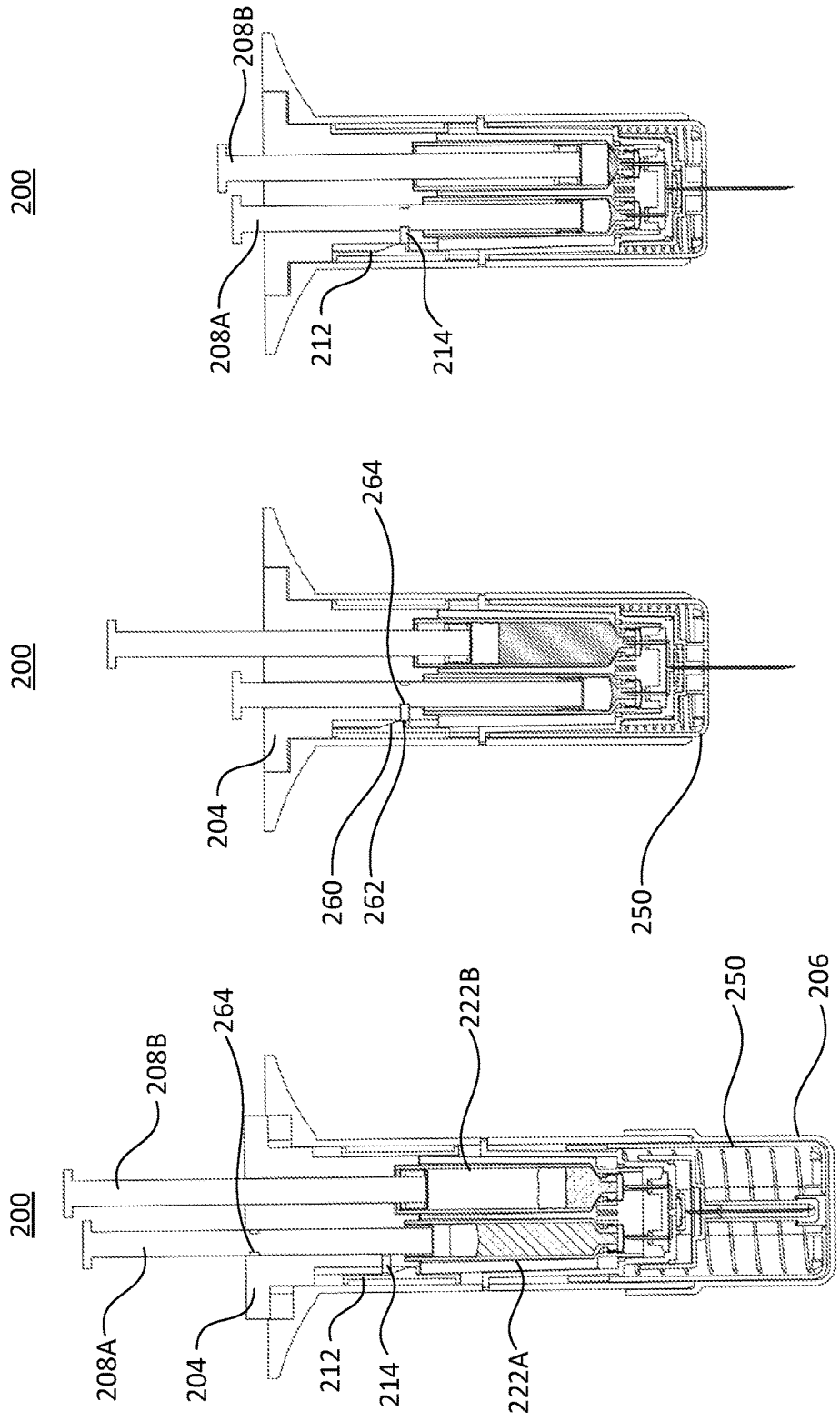

300

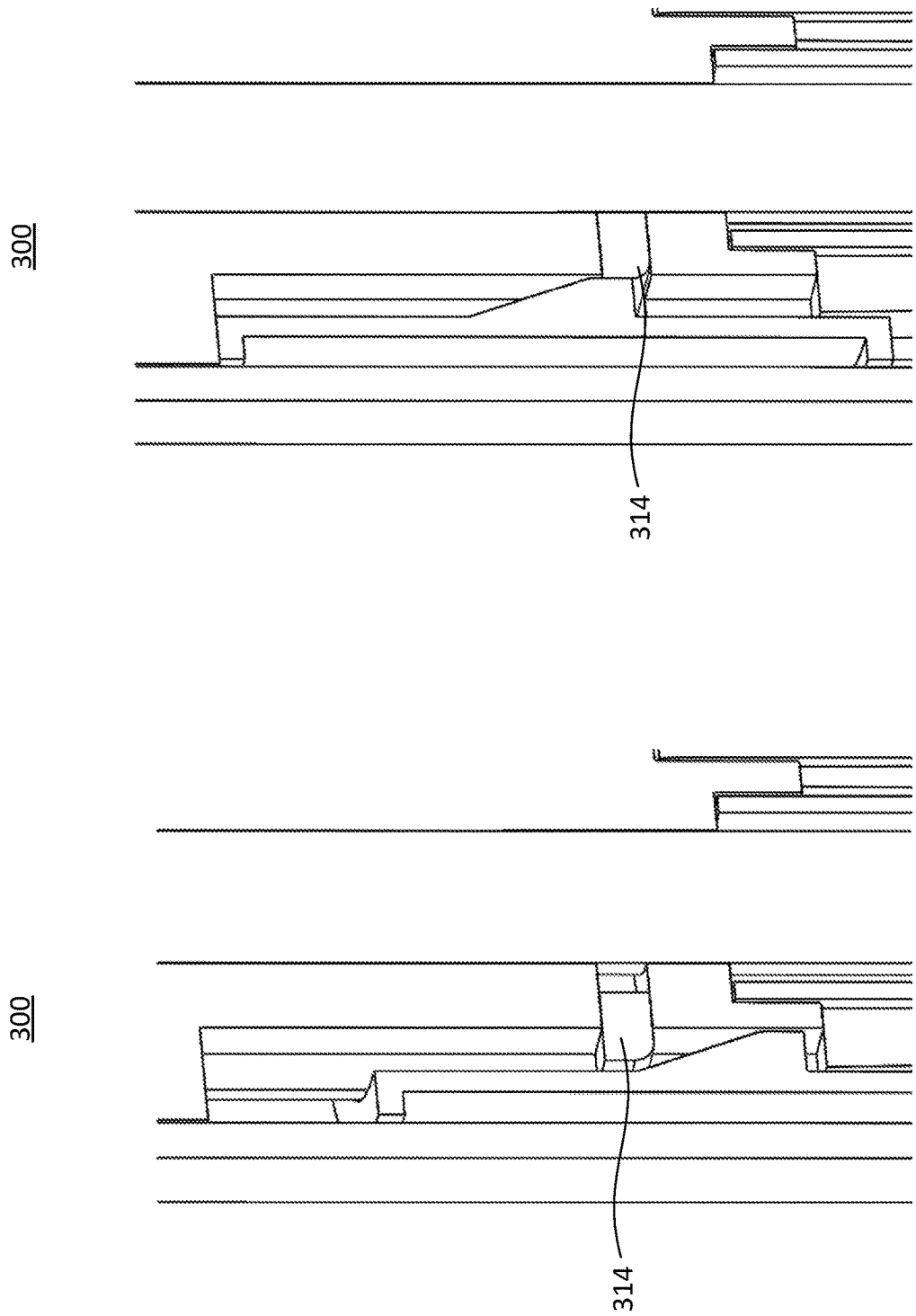

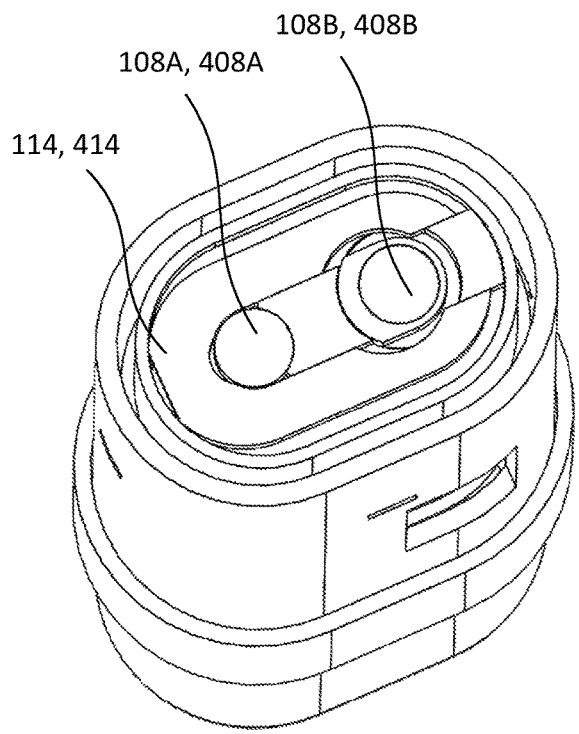
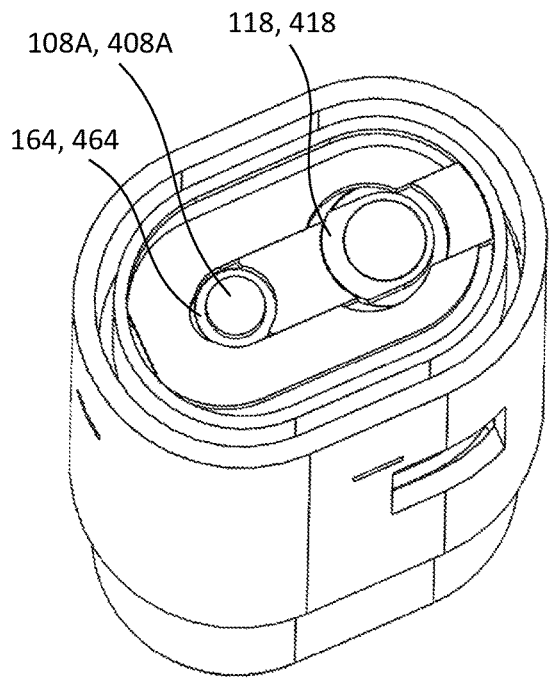
FIG. 10A
FIG. 10B
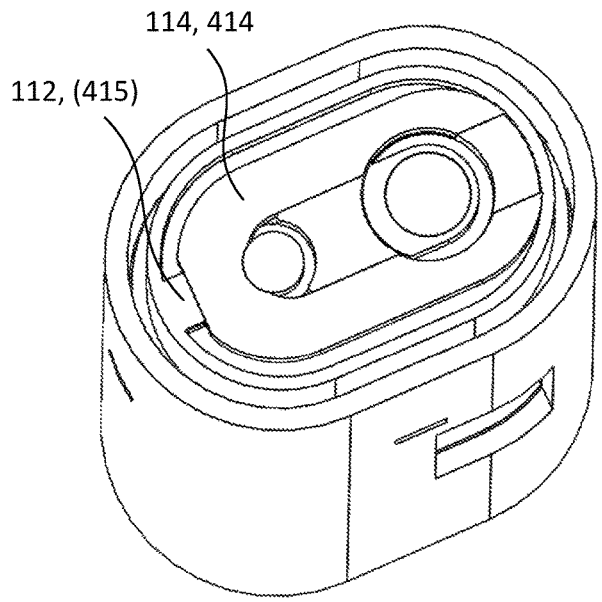
FIG. 10C

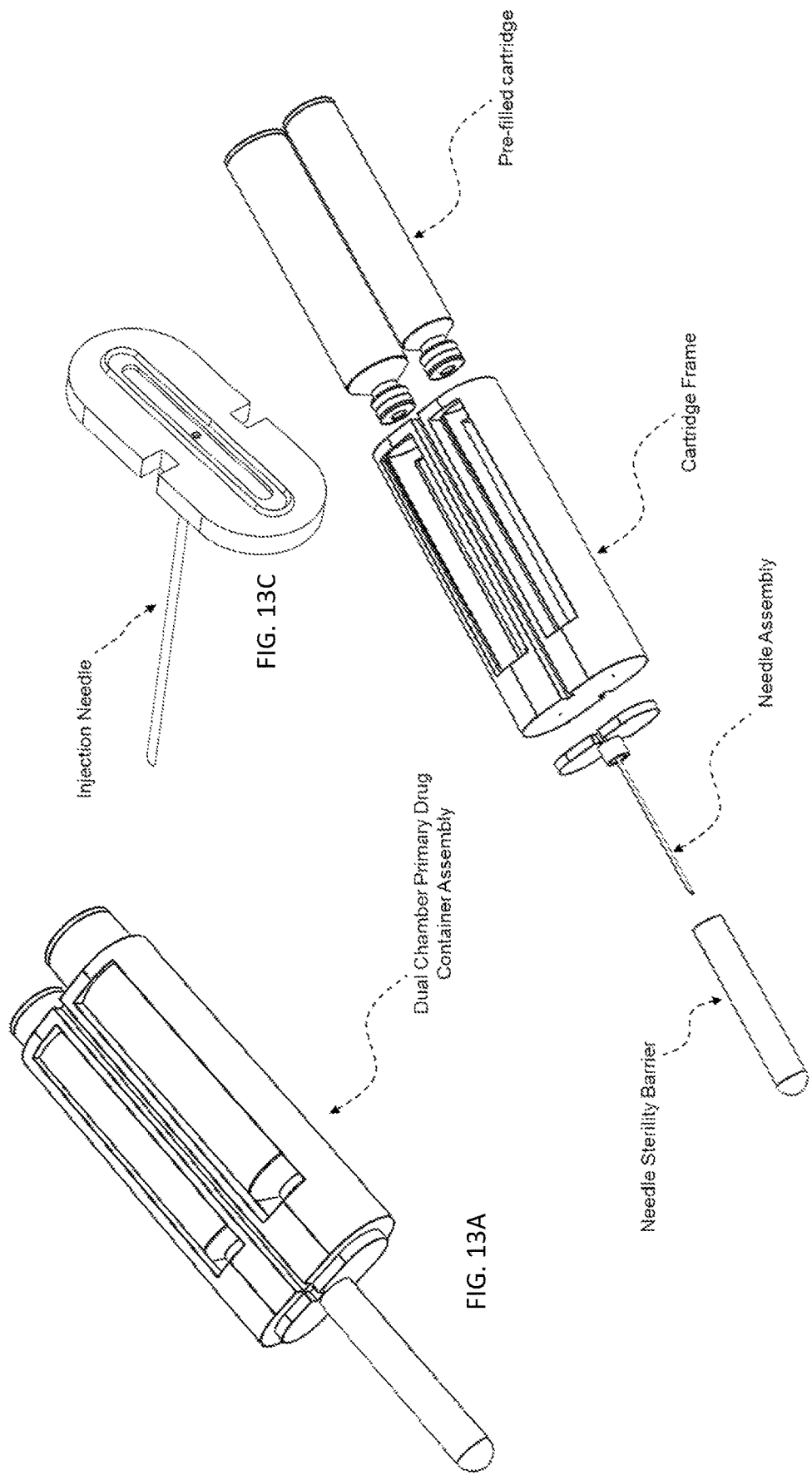

Microfluidic Mixing Channel

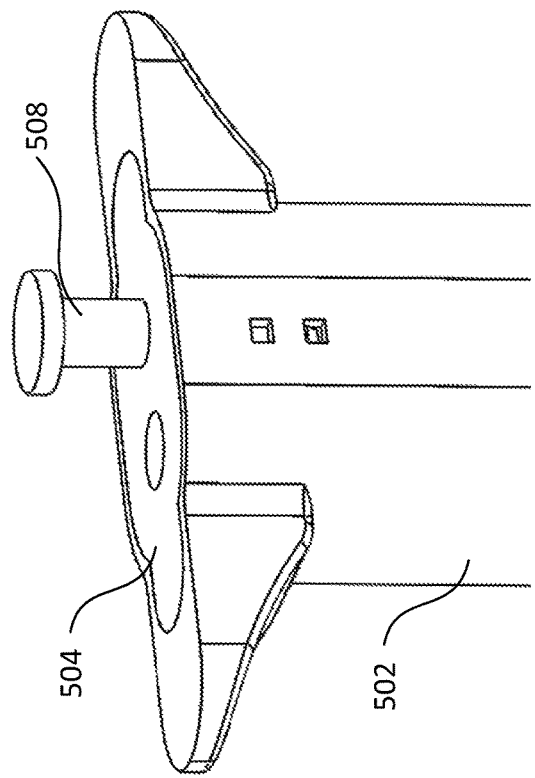
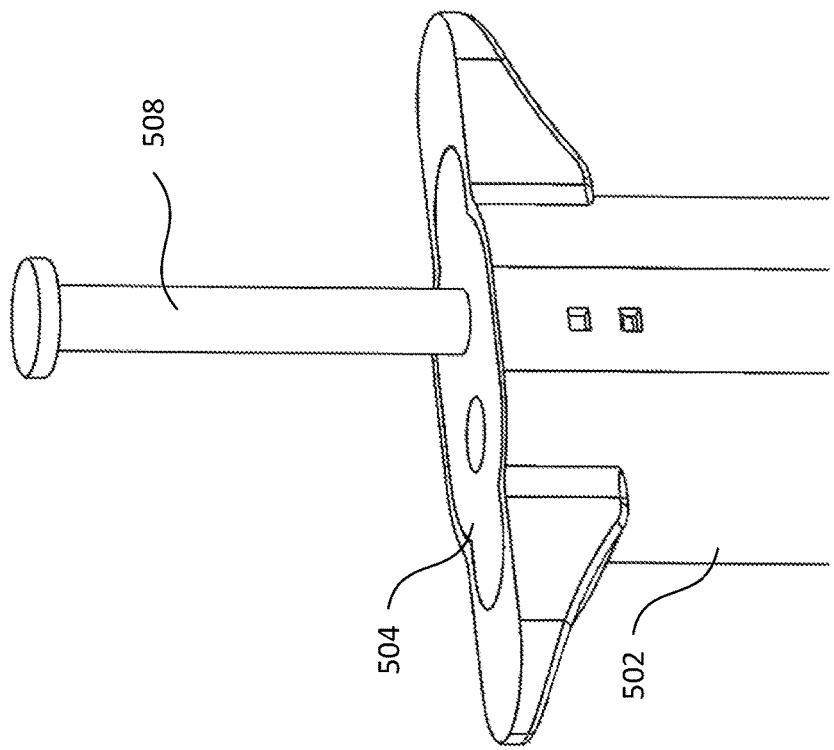
FIG. 15D
FIG. 15C

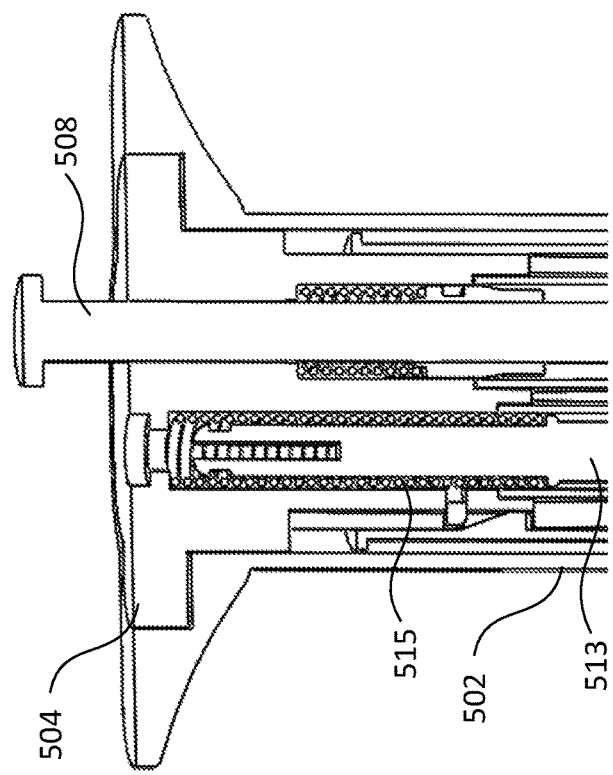
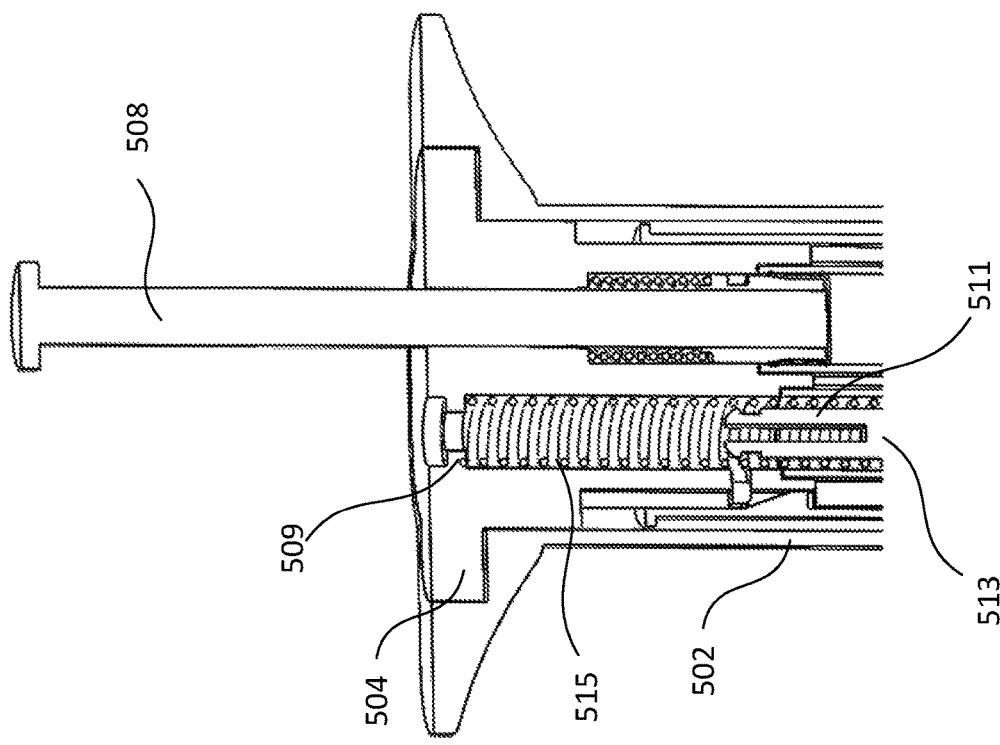
FIG. 16D
FIG. 16C

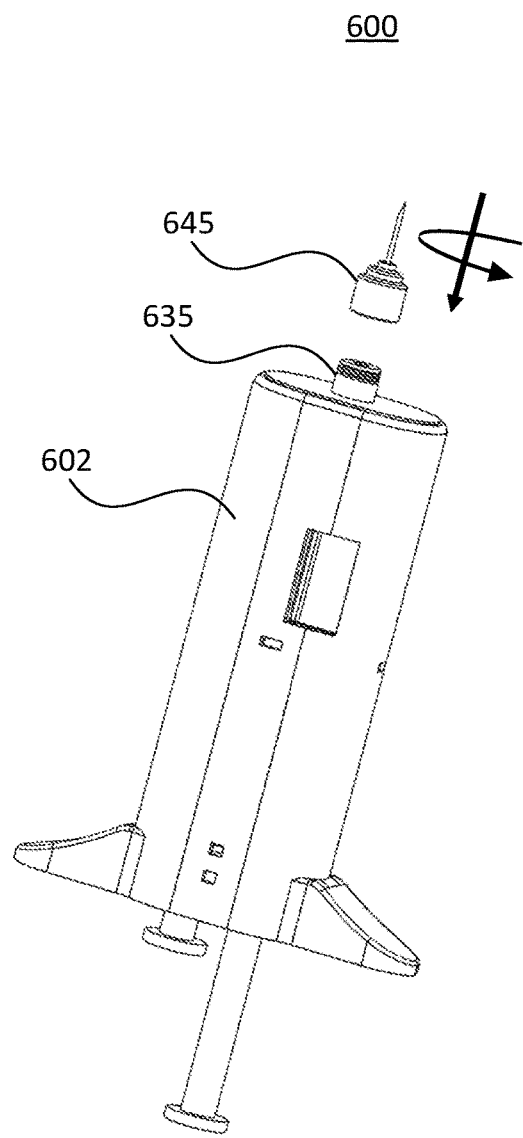
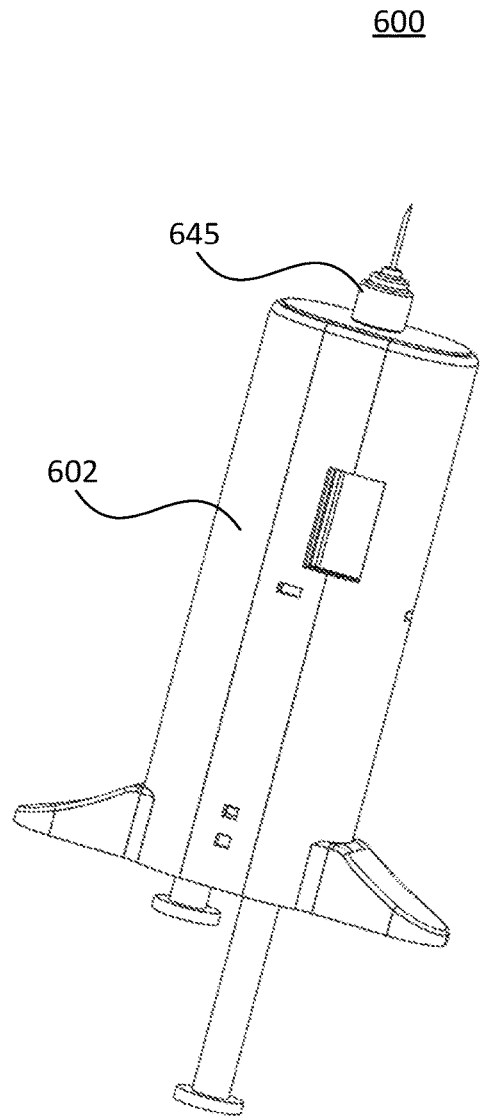
FIG. 17A
FIG. 17B

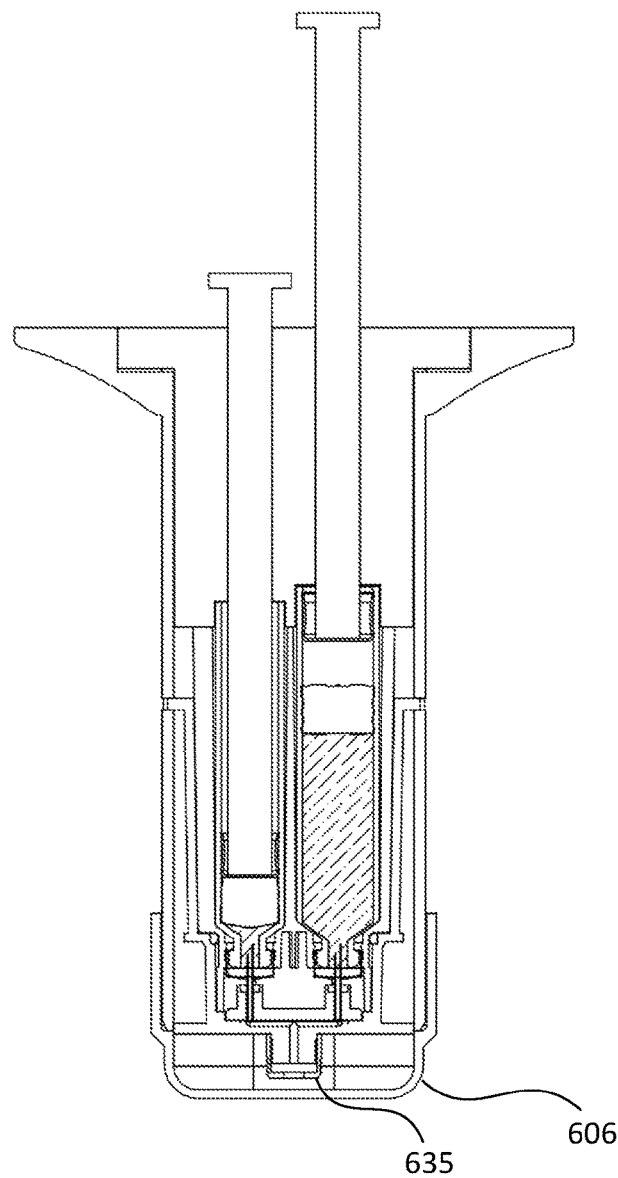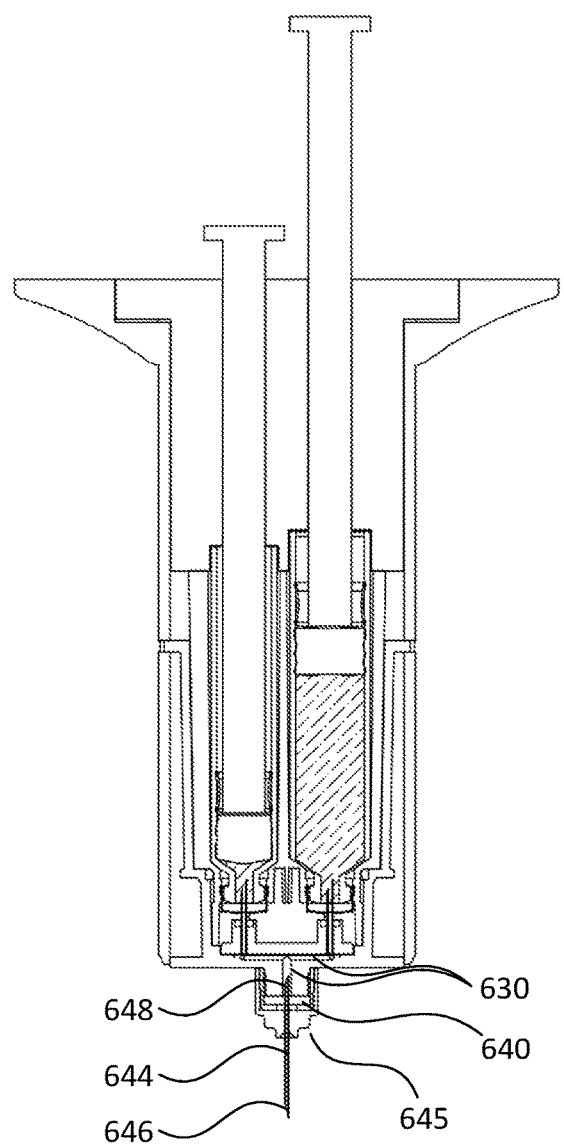
FIG. 17E
FIG. 17F

DYNAMIC MIXING AND DELIVERY SYSTEM FOR MIXING A THERAPEUTIC AGENT IN AN INJECTOR OR AUTOINJECTOR

CROSS-REFERENCE TO RELATED APPLICATIONS

This application claims the benefit of U.S. Provisional Patent Application No. 63/032,311 filed on May 29, 2020; which is herein incorporated by reference in entirety.

GOVERNMENT LICENSE RIGHTS

This invention was made with government support under U01 NS112125 awarded by National Institutes of Health. The government has certain rights in the invention.

FIELD OF THE INVENTION

The present invention relates generally to dual container devices for reconstituting medicament components or sequentially delivering medicament components.

BACKGROUND OF THE INVENTION

Dual chamber injector/autoinjectors are known for storing drug constituents separately until reconstitution at point of use. There are various benefits to therapeutics which may be preferred to be provided in a multi-chamber format. The drug may be more thermally stable, have a longer shelf life, or have other issues being in its aqueous form. Solubilizing drugs in liquid agents, suspending dry particles in liquids, or combining liquid-liquid solutions or suspensions thereof may be required for similar reasons.

In the field of use of multi-chambered injector/autoinjectors, there are also drug formulations where high-intensity and/or long duration mixing is needed after recombination of the drug constituents. This may be due to low solubility of the drug, poor surface energy or wettability of a powder or microparticle for dissolution. Other needs include making a suspension of particles homogeneously dispersed within a solvent, solving problems with caking of a dry phase requiring initial energy for dispersion, or poor miscibility making emulsification difficult. In some cases, speed and ease-of-use may be critical for rescue applications where an emergency treatment needs to be delivered very quickly and with very few steps. In this field of use, state-of-the-art devices typically rely on a user shaking the drug container to mix, dissolve, or suspend the drug. Preparation can also require multiple steps that include changing out needles, or moving drug and diluent from one container to another manually. As a result of these additional user-required step, users may experience: delays in treatment time, inadequately mixed drugs, or become generally dissatisfied with the experience of using the product. In other cases, drugs may be formulated in less ideal ways where users may be required to inject a higher dose volume, endure a less comfortable dosage form, a larger than desirable delivery needle, be exposed to additional solubilizing or stabilizing agents added to the formulation, or be required to make more frequent injections. There is significant motivation to create a device that can mix drugs which are otherwise difficult to solubilize, reconstitute, or suspend by re-combination alone.

The present application seeks to solve some of these identified problems as well as other problems that will become apparent to those skilled in the art.

SUMMARY OF THE INVENTION

Several embodiments of drug mixing and drug delivery devices are disclosed herein.

In one embodiment a mixing and drug delivery system comprises a housing configured to hold a first container and a second container, where in the first container contains a first medicament component and the second container contains a second medicament component; a first seal; a second seal; a seal opening component configured to open, remove or otherwise pierce the first seal and the second seal; a fluidic channel that allows for fluidic communication between the first and second containers once the seal opening component has caused each of the first and second containers to be altered from a sealed stated to an open state; a first plunger at least partially disposed within the first container and a second plunger at least partially disposed within the second container, wherein depressing the first plunger drives a portion of the first medicament from the first container through the fluidic channel into the second container to mix with the second medicament, and wherein the second plunger when depressed during a second transfer state causes a portion of the mixed medicament in the second container to transfer from the second container through the fluidic channel into the first container; a delivery seal disposed about a portion of the fluidic channel; and a delivery assembly having a delivery seal opening component and a delivery component, wherein the delivery seal opening component is configured to cause the delivery seal to alter from a sealed state to an open state, thus allowing the delivery assembly to be in fluidic communication with the fluidic channel.

It should be noted that the volume of the first container and the volume of the second container can be identical or differ in size.

The above noted mixing and drug delivery system embodiment can further include an actuation device that includes a stored energy source, whereupon actuating the actuation device causes the stored energy source to release and cause the second plunger to depress and force the mixed medicament disposed in the second container to flow out of the delivery assembly.

In some variations to the embodiment, the actuation device is coupled to a locking mechanism and upon actuating of the actuation device, the actuation device causes the locking mechanism to engage with the first plunger, thus preventing the first plunger from moving inwardly or outwardly with respect to the housing.

In some variations to the embodiment, there is no actuation device and the locking mechanism is associated with the first plunger, and whereupon engaging the locking mechanism prevents the first plunger from moving inwardly or outwardly with respect to the housing during the delivery step.

The embodiment above can further include a first plunger rod associated with the first plunger and a second plunger rod associated with the second plunger.

Some variations can include a plunger rod connecting mechanism associated with the first plunger rod and second plunger rod, and whereupon engaging the plunger locking mechanism causes the first plunger and second plunger to move in unison. This can come in the form of a sliding component or alternatively each of the plunger rods can have an extended flange that when rotate interface with each other and when depressing one flange causes the other to be depressed.

A needle shield assembly can be coupled to the actuation device in some configurations. The needle shield assembly can also function as a bump trigger to actuate the actuation device.

Alternatively a side button can be coupled and/or part of the actuation device which causes the locking mechanism to lock the first plunger in place and prevent it from moving inwardly or outwardly.

The actuation device can further be configured to release a stored energy source associated with the second plunger and configured to drive the second plunger.

In some configurations, the needle shield assembly causes the delivery assembly to cause the delivery seal to alter from a sealed state to an open state.

In several embodiments the first container and the second container are aligned side-by-side to each other with both distal ends pointing in the same direction.

The first and second medicaments can be in dry or liquid form.

In another embodiment, the mixing and drug delivery system can include a safety release disposed about the proximal end of the first container. This safety release can cause a transfer spring to release and to engage with and force a driver to move the plunger, which causes the medicament in the container to transfer out through the fluidic channel.

The mixing and drug delivery system can further include a single plunger rod associated with the second plunger, and whereupon depressing the plunger rod causes a portion of mixed medicament to transfer to the first container and recompress the transfer spring. Once the plunger rod is released, the recompressed transfer spring can again release energy causing the driver to automatically depress the first plunger and transferring a portion of the mixed medicament back into the second container. This depressing of the plunger and releasing can cause the transfer to go back and forth each time it is depressed and released.

In some configurations, when depressing the first plunger it drives a portion of the mixed first and second medicament disposed in the first container through the delivery assembly once the delivery seal is in an open state.

Likewise, when depressing the second plunger it can drive a portion of the mixed first and second medicament disposed in the second container through the delivery assembly. Thus, a first, second or simultaneous depressing of the plungers using plunger rods once a delivery assembly is fluid communication drives any medicaments out.

The seal opening component can be comprised of at least one or more mixing needles.

The mixing needle can be in fluid connection with the fluidic channel. The mixing needle can be supported by a mixing needle hub. In some variations, there can be sterility seal that the mixing needle is partially disposed therein during a stored state.

The seal opening component can be affected by a fluid communicating mechanism extending outward from the housing and when depressed into the housing causes fluid communication between the first and second containers.

With regards to the first and other embodiments noted, the first container, second container, first plunger, second plunger and fluidic channel are configured to transfer a portion of the mixed medicament back and forth into each of the first and second containers multiple times through a plurality of transfer states.

The drug mixing and drug delivery system embodiments can further include a first sterility cap disposed on an upper portion of the first container and a second sterility cap disposed on an upper portion of the second container.

The drug mixing and drug delivery system embodiments can further include an upper sterility barrier disposed about the first and second containers and configured to help form a sterility volume. They can also include a lower sterility barrier disposed about the delivery assembly and configured to help form a second sterility volume.

The first or second plunger rods can have a notch formed therein and configured to interface with a locking mechanism or release mechanism.

In yet another embodiment a drug mixing system comprises: a housing configured to hold a first container and a second container, where in the first container contains a first medicament component and the second container contains a second medicament component; a first seal; a second seal; a seal opening component configured to open, remove or otherwise pierce the first seal and the second seal; a fluidic channel that allows for fluidic communication between the first and second containers once the seal opening component has caused each of the first and second containers to be altered from a sealed stated to an open state; a first plunger at least partially disposed within the first container and a second plunger at least partially disposed within the second container, wherein depressing the first plunger drives a portion of the first medicament from the first container through the fluidic channel into the second container to mix with the second medicament, and wherein the second plunger when depressed during a second transfer state causes a portion of the mixed medicament in the second container to transfer from the second container through the fluidic channel into the first container; and a delivery seal disposed about a portion of the fluidic channel.

This embodiment can further include a delivery assembly having a delivery seal opening component and a delivery component, wherein the delivery seal opening component is configured to cause the delivery seal to alter from a sealed state to an open state, thus allowing the delivery assembly to be in fluidic communication with the fluidic channel. This delivery assembly can be attachable to a delivery connection. In some configurations the delivery connection is threaded and some configurations it can be luer lock or bayonet style connector.

For this embodiment when depressing the first plunger it can drive a portion of the mixed first and second medicament disposed in the first container through the delivery assembly once the delivery seal is in an open state.

For this embodiment when depressing the second plunger it can drive a portion of the mixed first and second medicament disposed in the second container through the delivery assembly once the delivery seal is in an open state.

For this embodiment when depressing the first and second plunger simultaneously it can drive the mixed first and second medicaments disposed in the first and second containers simultaneously through the delivery assembly once the delivery seal is in an open state.

The drug mixing system embodiment can also include a safety release disposed about the proximal end of the first container in some variations, even without having an integrated delivery assembly. This can be part of transfer actuator, which includes a safety release; a transfer spring; a driver; and a plunger rod. The safety release, transfer spring and driver can be associated with the first container. As noted in other embodiments, these can act to drive medicament out of the first container when the transfer spring is released. Again, the transfer spring can be recompressed when the medicament from the second container is driven back into the first container by depressing a plunger rod associated with the second container. Once the plunger rod is released the transfer spring is again released and the transfer from first to second container is accomplished again. This step can be repeated multiple times.

The delivery connection noted can be positioned about the fluidic channel.

In yet another embodiment, a drug medicament mixing system comprises: a housing configured to hold a first container and a second container, wherein the first container contains a first medicament component and the second container contains a second medicament component; a fluidic channel; a fluid communicating mechanism, whereupon actuating the fluid communicating mechanism causes the first container to be in fluid communication with the second container via the fluidic channel; and a transfer actuator.

In yet another embodiment, a drug medicament mixing system comprising: a housing configured to hold a first container and a second container, wherein the first container contains a first medicament component and the second container contains a second medicament component; a fluidic channel; a fluid communicating mechanism, whereupon actuating the fluid communicating mechanism causes the first container to be in fluid communication with the second container via the fluidic channel; and a first plunger rod associated with the first container and a second plunger associated with the second container.

The fluid communicating mechanism can extend partially out of the housing and upon depressing the fluid communicating mechanism initiates fluid communication between the first and second containers.

In yet another embodiment, a drug medicament delivery system comprising: a housing configured to hold a first container and a second container, wherein the first container contains a first medicament component and the second container contains a second medicament component; a fluidic channel; a delivery assembly having a delivery needle that is in fluid communication with the fluid channel; a sterility barrier having a delivery end of the delivery needle disposed partially therein; a first piercing needle in fluid communication with the fluid channel, and having a first sterility seal disposed about a portion of the end of the first piercing needle; and a second piercing needle in fluid communication with the fluid channel, and having a second sterility seal disposed about a portion of the end of the second piercing needle mechanism.

In yet another embodiment, a drug medicament delivery system comprises: a housing configured to hold a first container and a second container, wherein the first container contains a first medicament component and the second container contains a second medicament component; a fluidic channel; a first piercing needle in fluid communication with the fluid channel, and having a first sterility seal disposed about a portion of the end of the first piercing needle; and a second piercing needle in fluid communication with the fluid channel, and having a second sterility seal disposed about a portion of the end of the second piercing needle mechanism.

In yet another embodiment, a mixing and drug delivery system comprises: a housing configured to hold a first container and a second container, where in the first container contains a first medicament component and the second container contains a second medicament component; a first seal; a second seal; a first seal opening component configured to open, remove or otherwise pierce the first seal; a second seal opening component configured to open, remove or otherwise pierce the second seal; a fluidic channel that allows for fluidic communication between the first container and a delivery needle once the first seal opening component has caused the first seal to be altered from a sealed stated to an open state; the fluidic channel also allows for fluidic communication between the second container and the delivery needle once the second seal opening component has caused the second seal to be altered from a sealed stated to an open state; a first plunger at least partially disposed within the first container and a second plunger at least partially disposed within the second container, wherein depressing the first plunger drives a portion of the first medicament from the first container through the delivery needle, and wherein subsequently depressing the second plunger drives a portion of the second medicament from the second container through the delivery needle.

These embodiments and others are described in further detail below.

BRIEF DESCRIPTION OF THE DRAWINGS

The foregoing and other objects, features, and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

FIGS. 4A-D illustrate various close-up cross-sectional views of the medicament mixing device embodiments that include the transition of a delivery needle before and after it pierces a delivery seal, which enables delivery of the mixed medicaments;

FIGS. 7A-C illustrate various states of an alternative embodiment of the mixing and delivery device, where the delivery components are manually operated.

FIGS. 8A-C illustrate another variant of the mixing devices already described, where the plunger rod is devoid of a plunger rod lockout feature;

FIGS. 10A-C illustrate various cross-sectional views of the release slider engaging with the plunger rod detent;

FIGS. 13A-C illustrate a delivery attachment device for mixing device that includes a fluidic channel disposed therein;

FIGS. 15A-D illustrate exterior views of another embodiment that includes a single manual plunger rod with a return transfer mechanism;

FIGS. 16A-D illustrate corresponding cross-sectional views of the FIGS. 15A-D;

FIGS. 17A-G illustrate various states of a device that includes an attachable and detachable delivery mechanism;

DETAILED DESCRIPTION OF THE INVENTION

To provide clarity, the applicants would like to provide context around certain terms used throughout this description that is in addition to their ordinary meaning.

Distal or distal end primarily refers to the end of the device opposite of that having the plunger rod. In contrast, proximal or proximal end refers to the end of the device having the plunger rods. For example, the distal end of the delivery needle would be the end to furthest from the plunger rod end of the device, while the proximal end of the delivery needle would be the closest to the plunger end of the device.

First purposes of this application the term container can include any component that is configured to hold a volume. For example, a cartridge, pre-filled syringe, a vial and so forth would be considered a container.

As noted, there is a need to improve upon drug mixing devices to allow for drug formulations where high-intensity and/or long duration mixing is needed after recombination of the drug constituents. The inventors, who created the embodiments herein, have provided solutions to at least this noted problem as well as other problems that will become apparent upon reading this description.

Figure 1A:
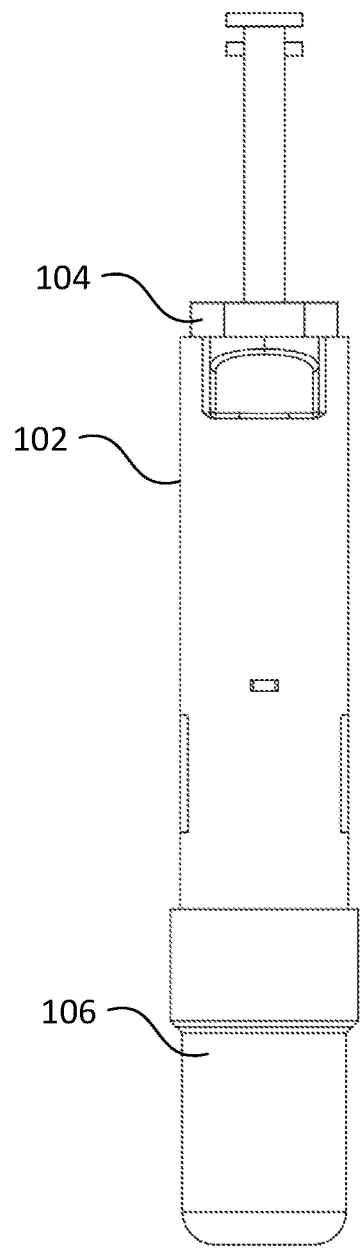
FIGS. 1A-J illustrates various states a medicament mixing and delivery device configured to have a plurality of medicament transfer states.
Figure 1B:
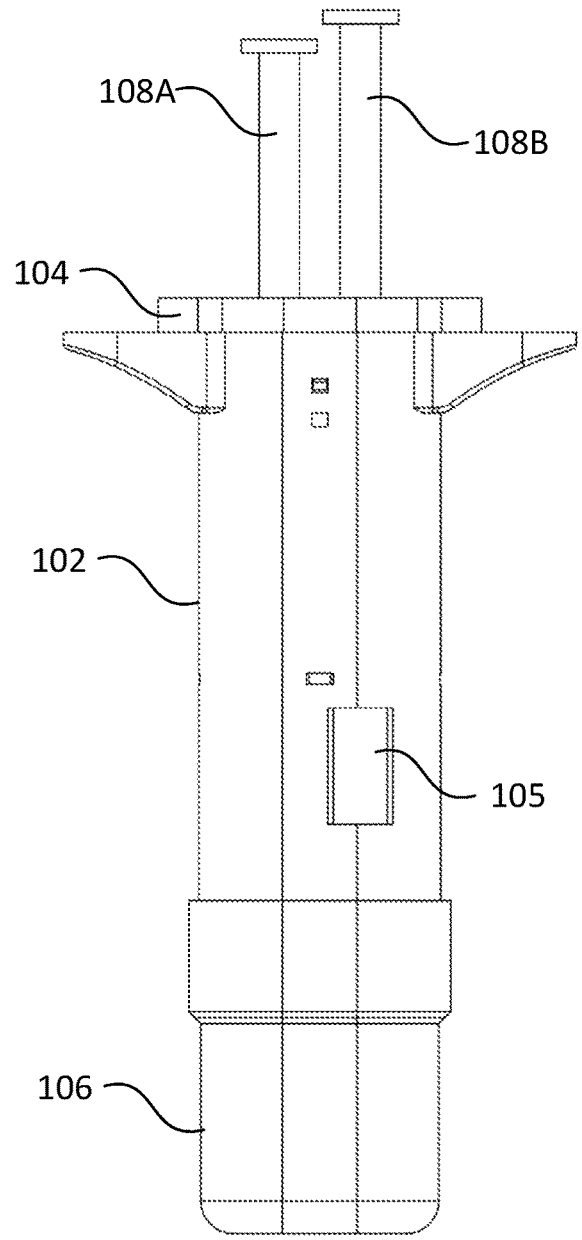

One embodiment to solve the above problem includes a combination medicament mixing and delivery device 100 as shown in various states in FIGS. 1A-J. FIGS. 1A and 1B illustrate a side view and front view of mixing and delivery device 100, which includes housing 102, a drive mechanism housing 104, a viewing aperture 105, a cap 106, and plunger rods 108A, 108B.

Figure 1C:
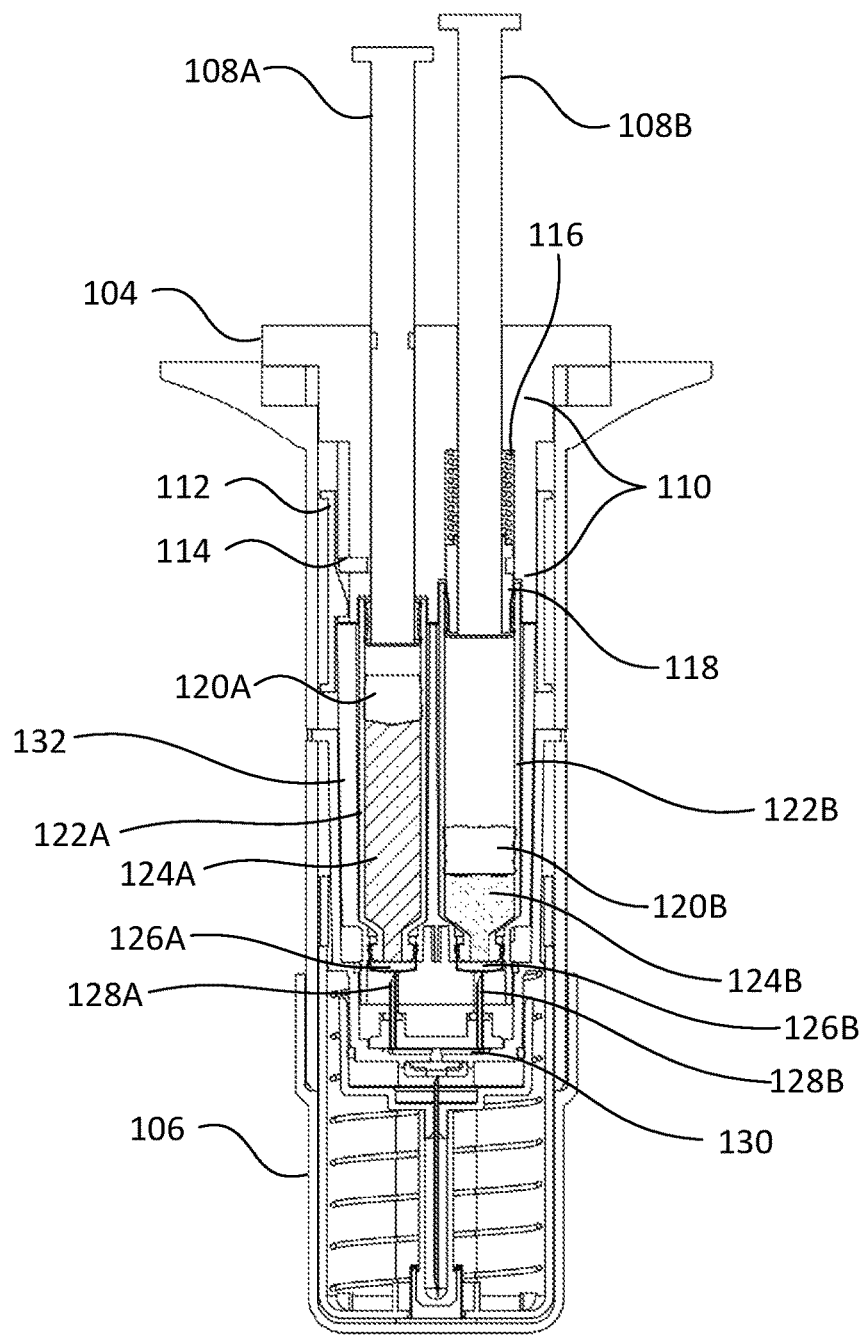
Figure 2A:
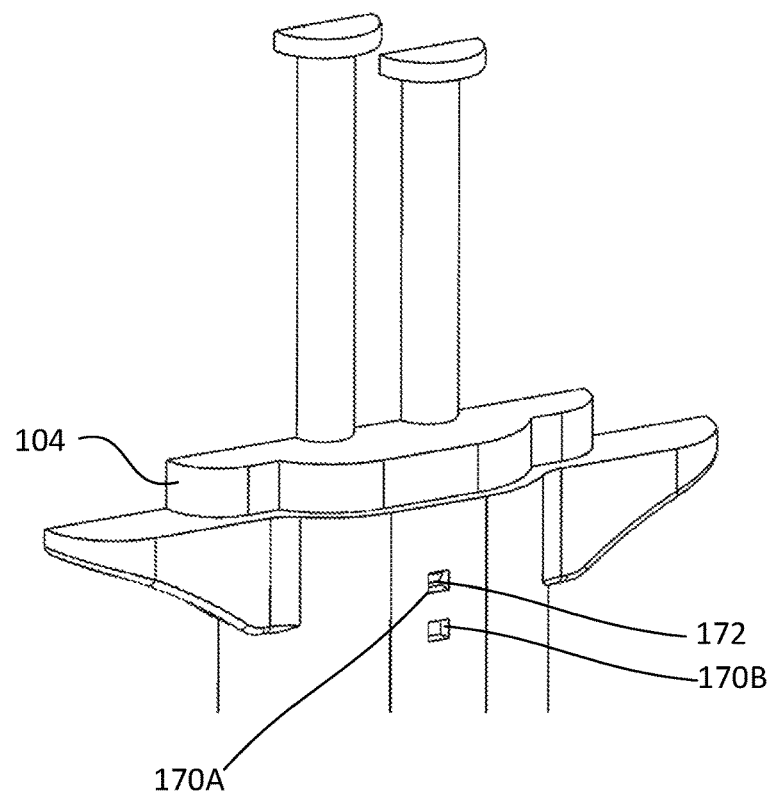
FIGS. 2A-B illustrates a drive mechanism housing lockout feature associated with several of the embodiments described herein.
Figure 2B:
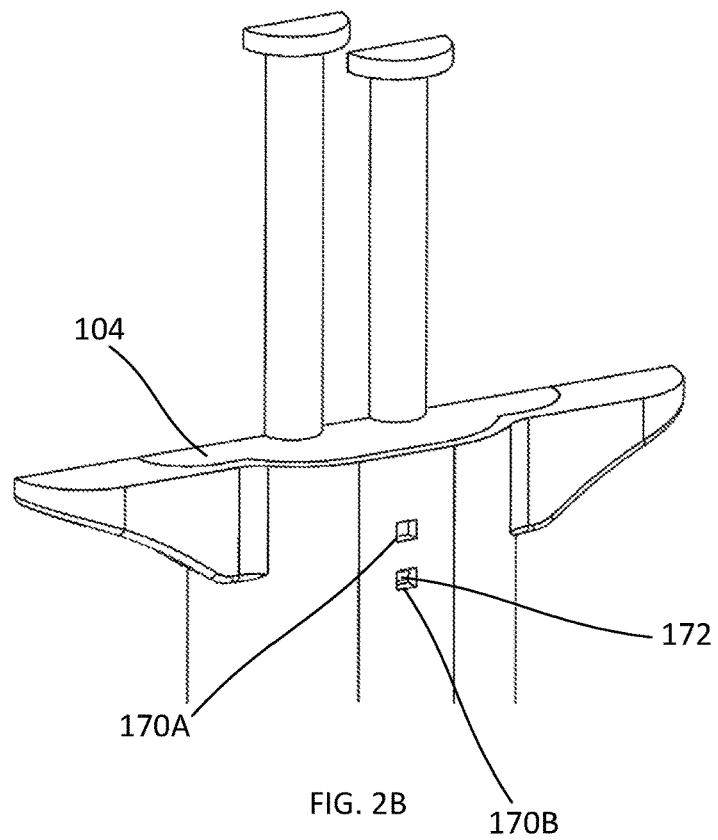

FIG. 1C is a cross-sectional view of mixing and delivery device 100 in a stored state. Disposed within drive mechanism housing 104 is drive mechanism 110, which includes a delivery spring 116 and a delivery piston 118. Disposed within housing 102 includes a container holder 132, which is configured to hold a first medicament container 122A and a second medicament container 122B. Each medicament container 122A, 122B has a first or second plunger 120A, 120B and first or second plunger rod 108A, 108B associated with it. each medicament container is configured to hold a first or second medicament component (124A, 124B). While in the stored state the first and second medicament components (124A, 124B) are fluidly incommunicated from each other. This state is maintained until 104 is depressed. 104 is held up by a snap feature 172 interfacing with a first notch 170A formed in the housing 102 as shown in FIG. 2A. When 104 is depressed the snap feature 172 releases until it snaps into notch 170B as shown in FIG. 2B. The snap feature 172 can be a passive or one-way snap. This holding and snap mechanism shown in FIGS. 2A-B can be applied to several of the embodiments described herein and not just 100 alone.

Figure 1D:
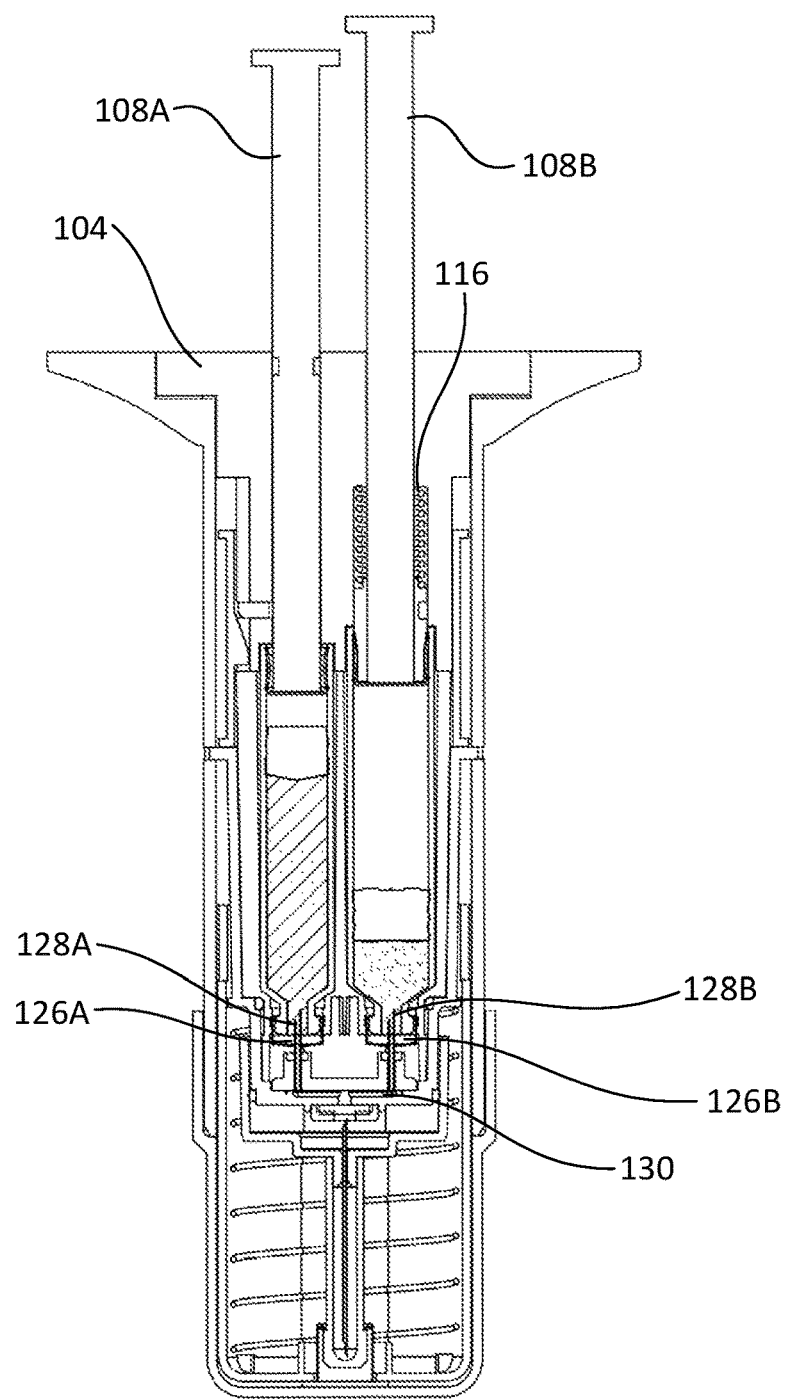
Figure 3B:
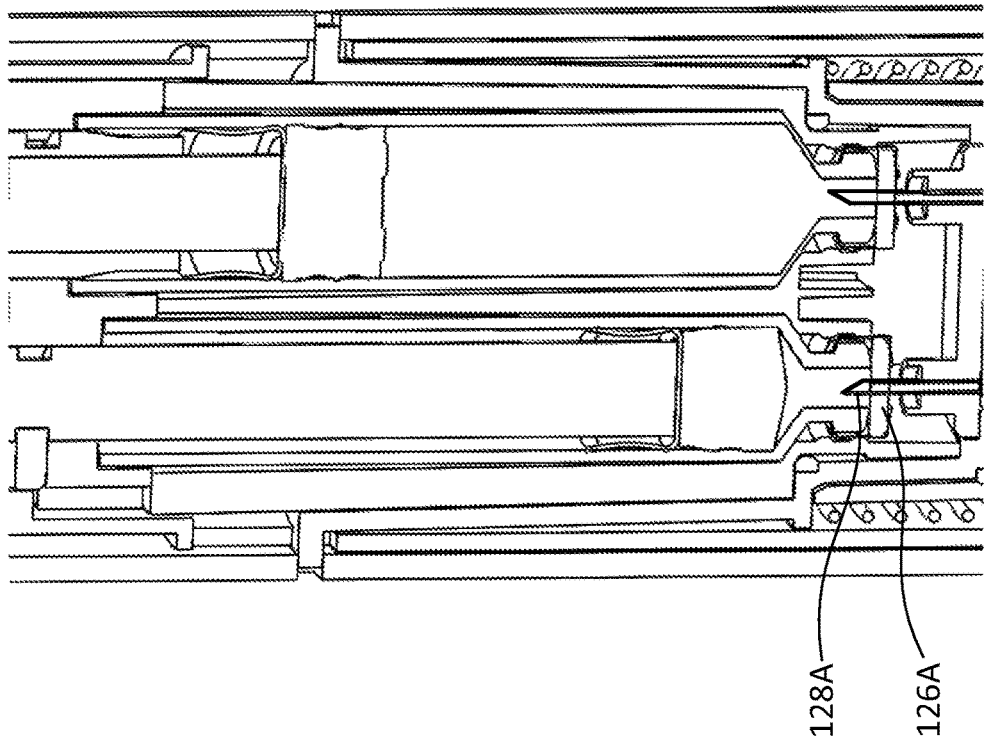
FIGS. 3A-B illustrates a close-up cross-sectional view of a medicament mixing device embodiment in a stored state and mixing state.
Figure 3A:
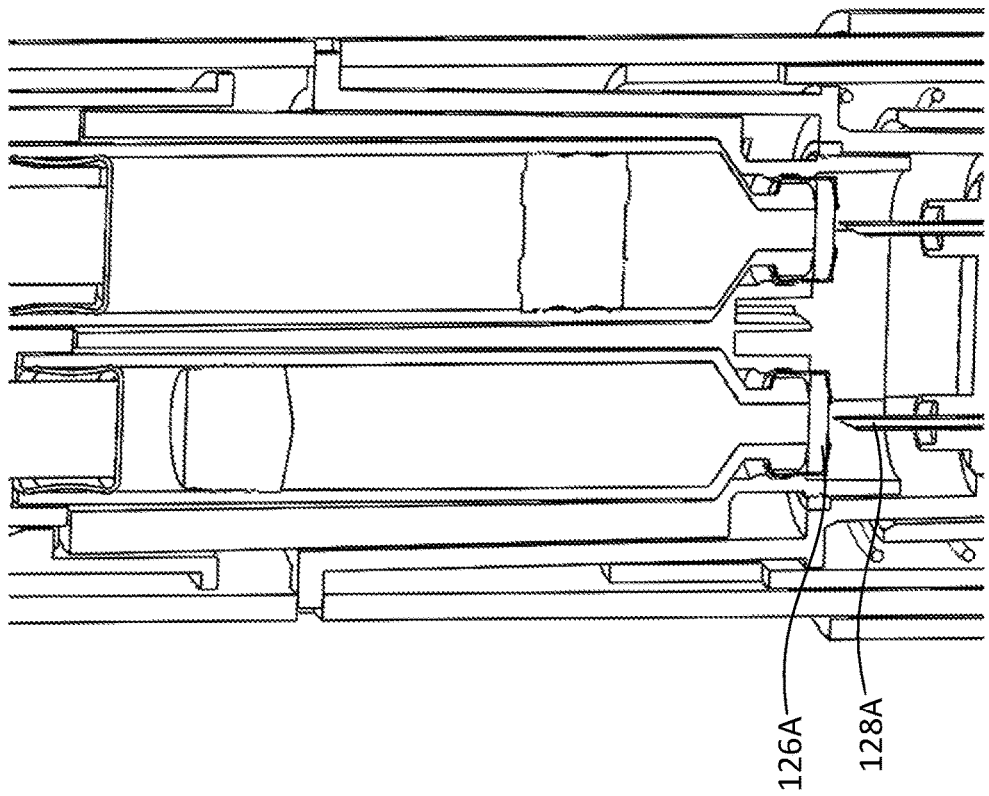
Figure 4B:
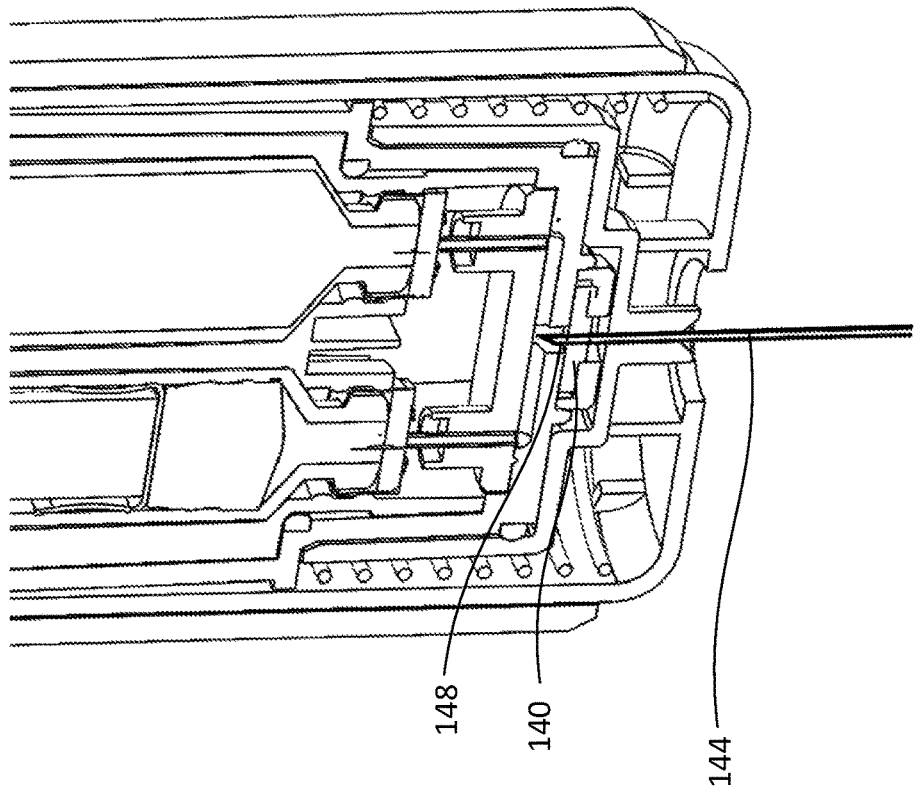
Figure 4A:
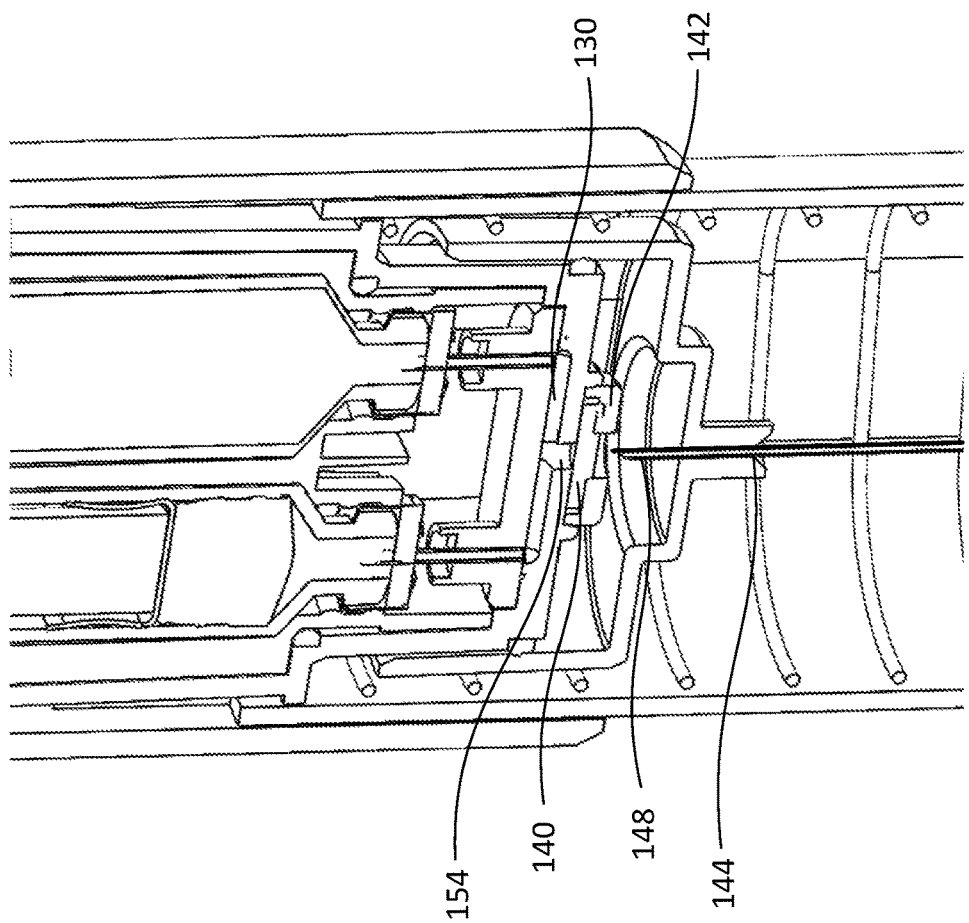

As shown in FIG. 1C, first container 122A and second container 122B each include a first container seal 126A and second container seal 126B respectively. A mixing needle 128A and mixing needle 128B are configured to pierce 126A and 126B to cause fluid communication between each container through the fluidic channel 130. As noted, once 104 is depressed, as shown in FIG. 1D, mixing needles 128A, 128B pierce through first and second container seals 126A, 126B and enable fluid communication between the first and second containers 122A, 122B. This can be referred to as the mixing initiation phase. FIGS. 3A-B illustrate close-up cross-sectional views of a medicament mixing device embodiment in a stored state and mixing state, including the before and after of the mixing needles 128A, 128B piercing the respective container seal 126A, 126B.

Figure 1E:
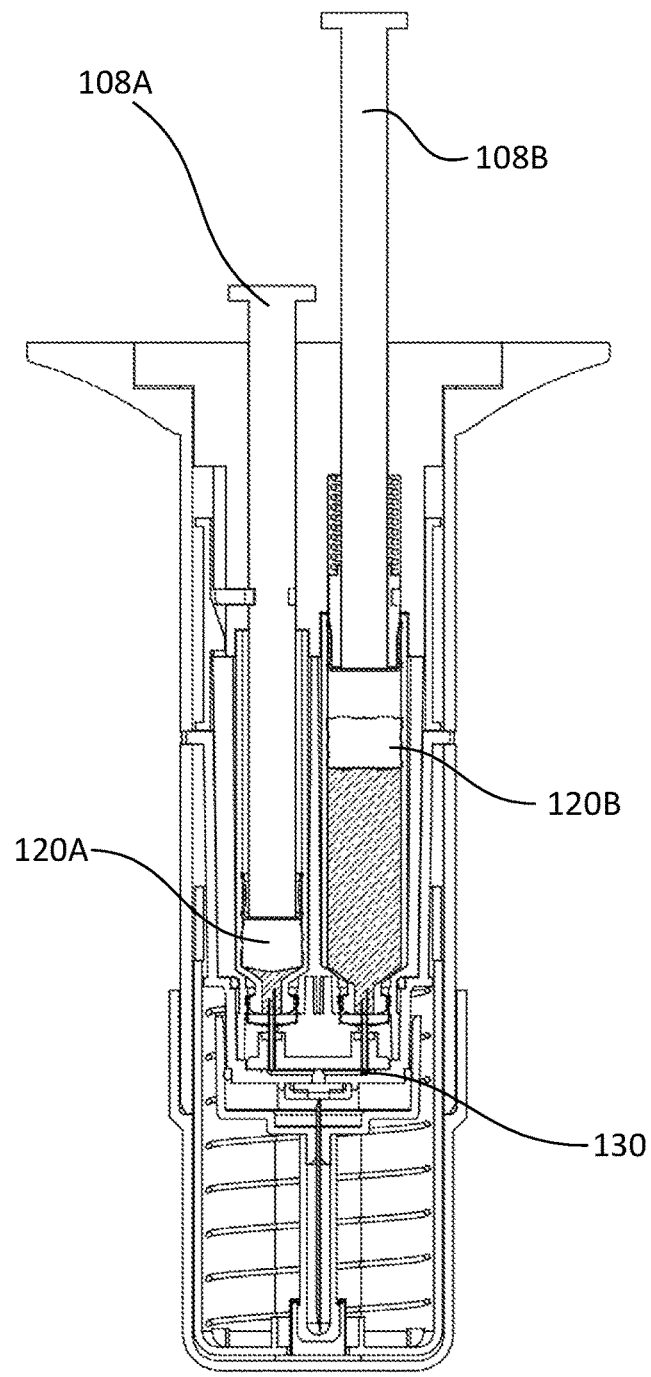

FIG. 1E illustrates plunger rod 108A being depressed onto plunger 120A which drives the first medicament component 124A into the second container 122B and begins mixing with second medicament component 124B. It should be noted that second medicament component 124B can be in a liquid or dry form, whereas first medicament component 124A is generally provided in a liquid form. The plunger 120B can rise to expand the internal volume of the second container 124B to receive the first medicament component. This can also be referred to as a first transfer or first transfer state of medicament components from one container to another container.

Figure 1F:
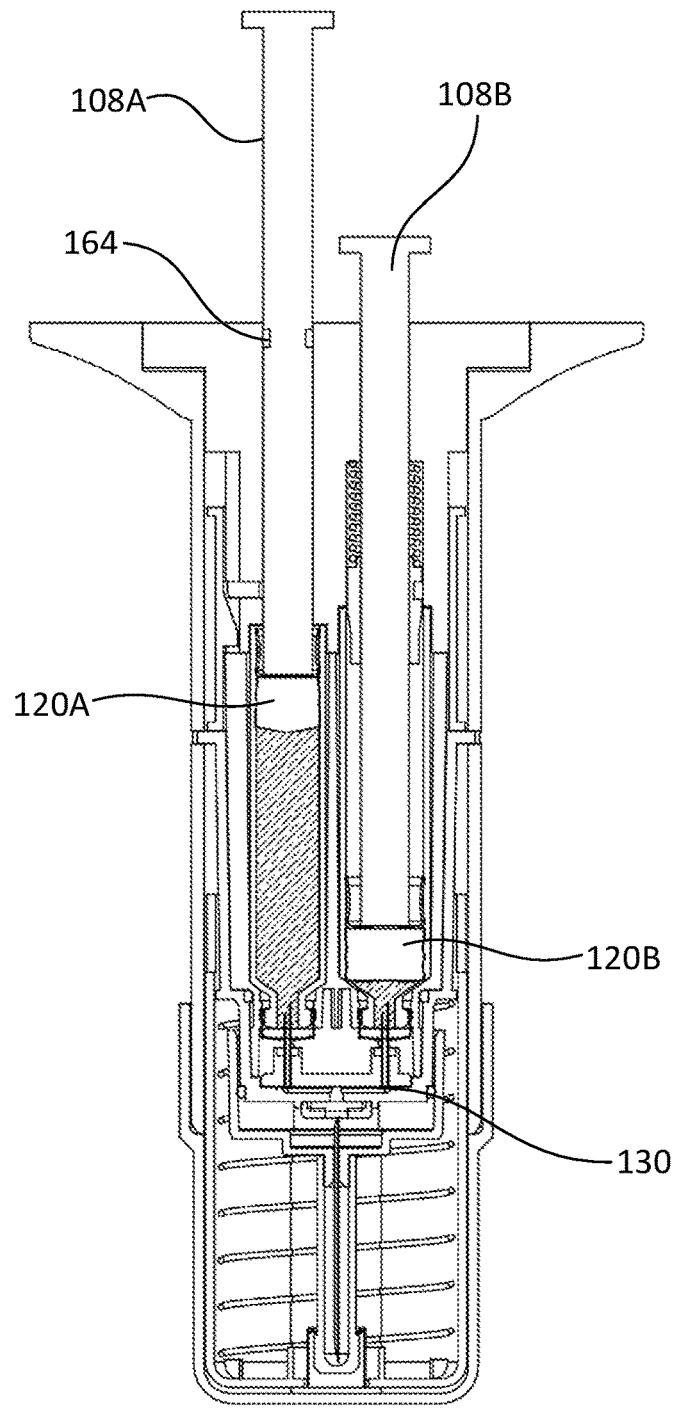

In FIG. 1F, a second transfer state is illustrated, whereby depressing plunger rod 108B, it forces plunger 120B in a distal direction and forces at least a portion of the mixed medicament components through the fluidic channel 130 back into the first container 122A.

Figure 1G:
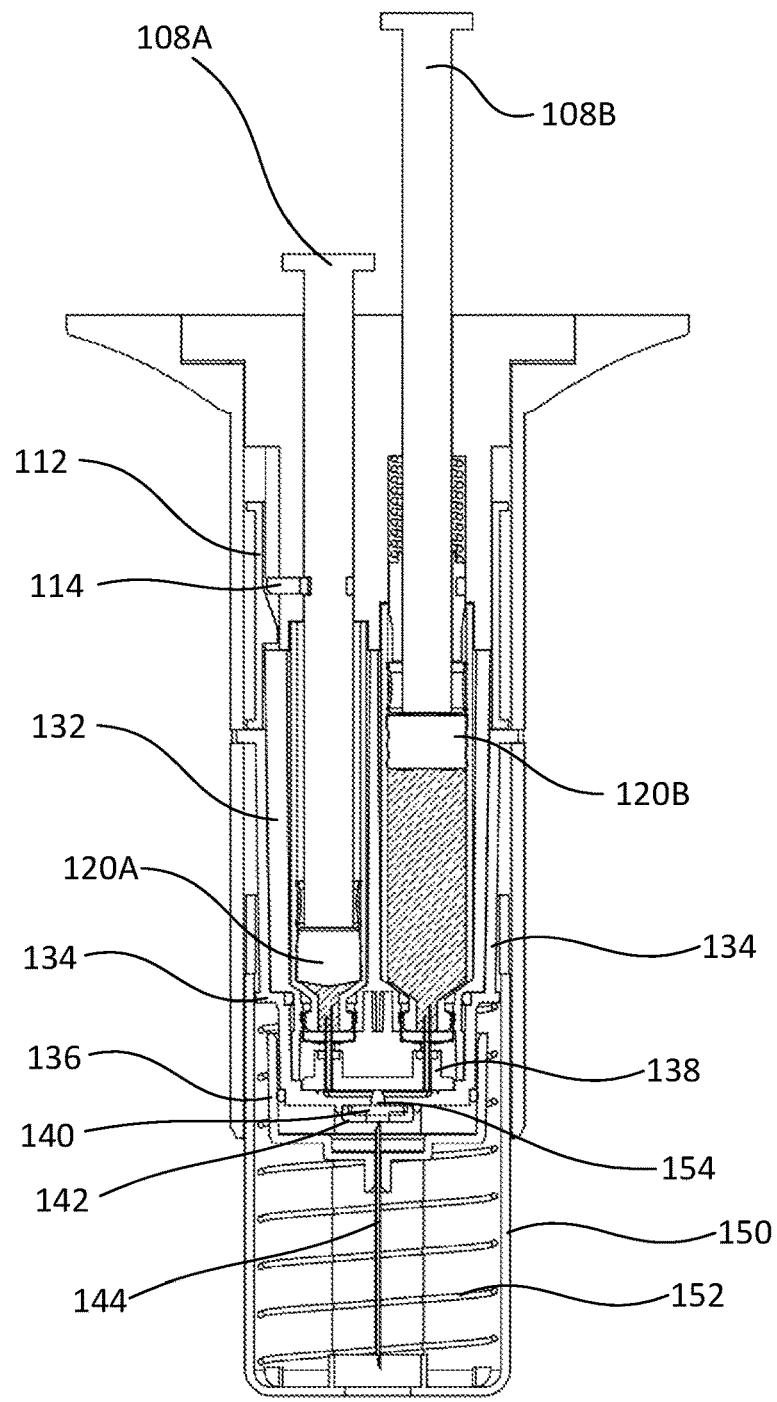

In FIG. 1G another transfer state takes place, this time depressing plunger rod 108A again applying force to plunger 120A to force the mixed medicament currently in the first container 122A back into the second container 122B back through the fluidic channel 130. It should be readily understood that a plurality of transfers can occur back and forth between the first and second containers multiple times thus enhancing the speed and quality of the medicament mixing process. A viewing aperture can used to view into one and/or both of the containers for confirmation that the mixed medicament is in a ready state to be delivered or otherwise transferred.

Figure 1H:
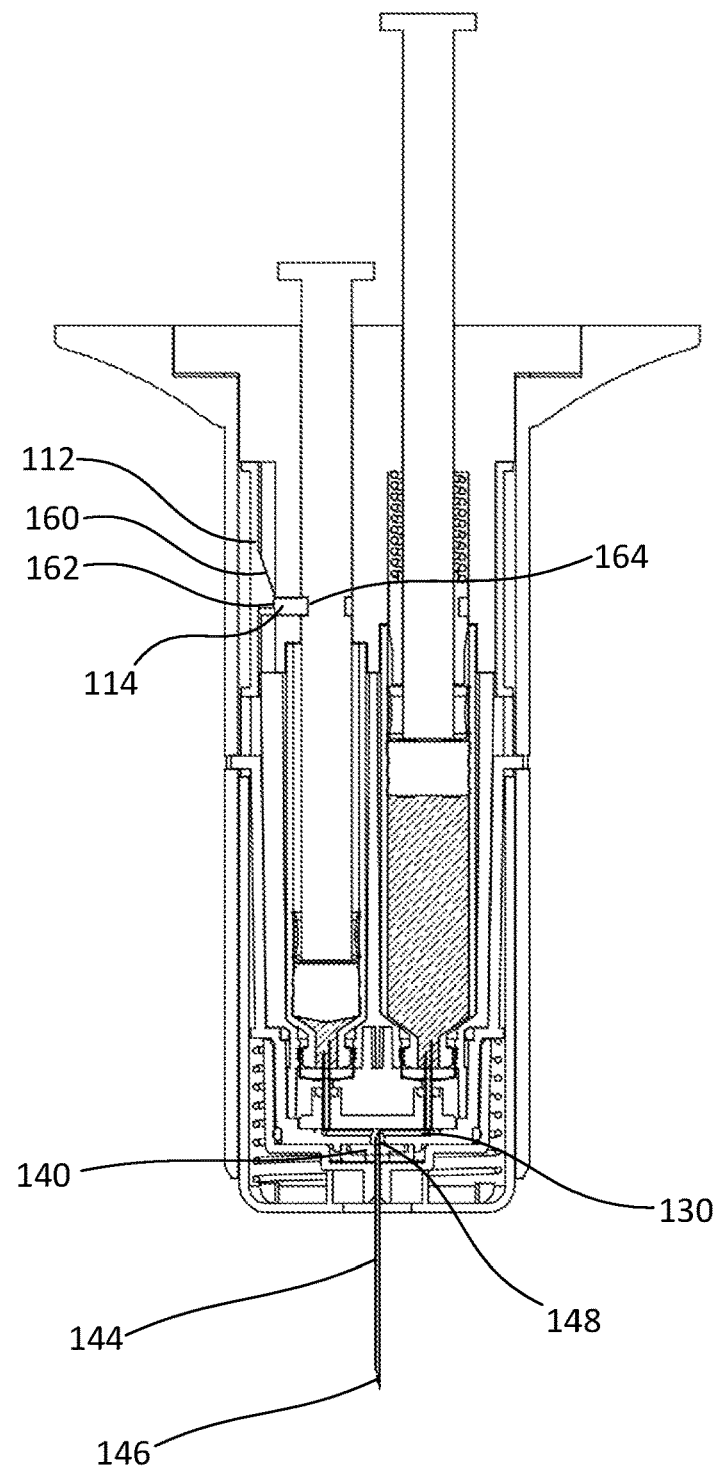

Once the medicament is fully mixed, solubilized, or suspended, and ready to administer, the cap 106 can be removed to expose the needle shield 150, which in device 100 also functions as a trigger to cause or actuate several functions. Firstly, it locks the first plunger rod into place as the upward or proximal motion of the needle shield pushes on the delivery collar 112, which has a delivery collar ramp edge 160 that causes the release slider 114 to transfer laterally over into the plunger rod detent 164 and fix into place once the delivery collar protrusion end 162 is fully engaged behind 114. This is locking the plunger rod step is shown in FIG. 1H.

Secondly, it causes the piercing end 148 of the delivery needle 144 to pierce through the delivery seal 140 that is held in place by a delivery seal cap 142. This delivery seal exposes the fluidic channel 130 to the delivery needle once in an open and/or pierced state and can allow the mixed medicament from the second container to flow through and out of the delivery needle 144 at the delivery end 146. In one embodiment of the device 100, a fluidic channel delivery interface 154 is formed about a portion of the fluidic channel 130 so as to receive the piercing end 148 of the delivery needle 144, as shown.

Figure 1I:
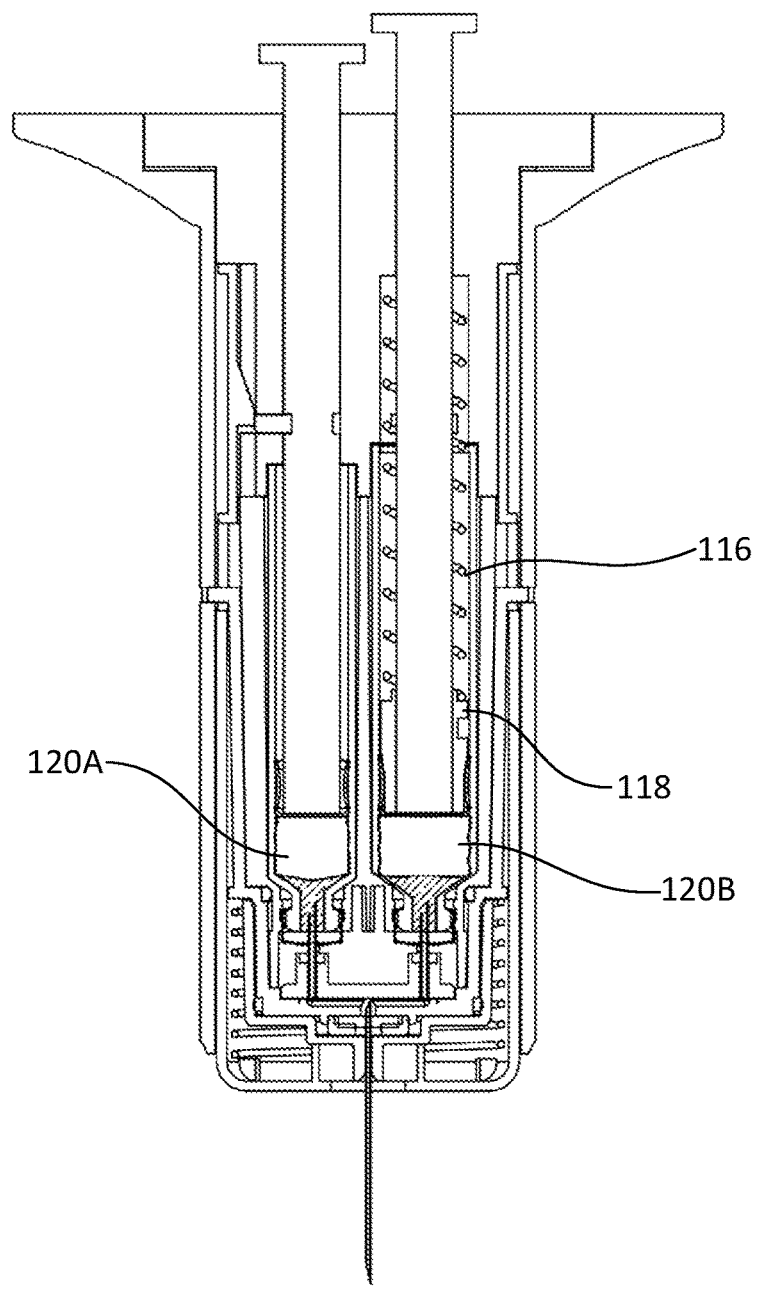
Figure 1J:
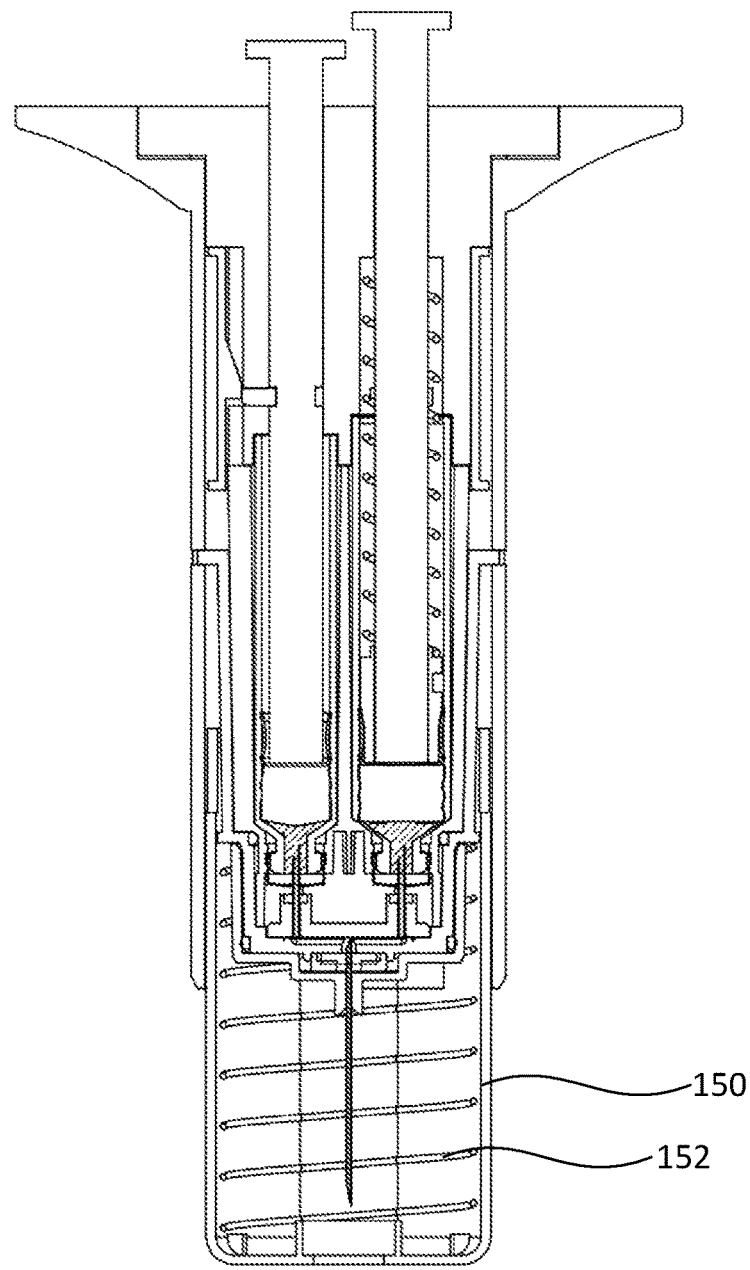

Thirdly, it causes the energy stored in the delivery spring 116 of the drive mechanism 110 to release and drive the mixed medicament now in the second container through the fluidic channel and out of the delivery assembly comprised of the delivery needle 144, which is held in place by the delivery hub 136. FIG. 1I illustrates delivery spring 116 in an extended state, which drives or forces the delivery piston 118 distally onto plunger 120B and causes the mixed medicament disposed therein to exit through the delivery needle 144 as noted.

Once the mixed medicament has been delivered out the delivery needle 144, the needle shield spring 152 can extend the needle shield outward to cover the delivery needle. This needle shield can then be locked into place by known methods, which are not the focus of this description.

In review of the above embodiment, device 100 is shown to enable a user to transfer back and forth medicament components from a first medicament container to a second medicament container a plurality of times until they are fully mixed and ready for delivery. Additional embodiments described below will illustrate variations of the embodiment above, while maintaining some of the same principles of an improved medicament mixing device. Variation embodiments of the mixing device can include a delivery assembly, or a version configured to receive a delivery assembly, can include auto-injector like features, or be manually delivered, and can also include semi-automatic mixing features. These and other features will be described below.

FIGS. 4A-D illustrate various close-up cross-sectional views of the medicament mixing device embodiments that include the transition of a delivery needle before (FIGS. 4A, 4C) and after (FIGS. 4B, 4D) it pierces a delivery seal, which enables delivery of the mixed medicaments. Here one can see the delivery seal 140, disposed about the fluidic channel delivery interface 154. As the piercing end 148 of the delivery needle 144 passes through the delivery seal 140 it engages with the fluidic channel delivery interface 154 and allows for open fluid communication with fluidic channel 130.

Figure 5A:
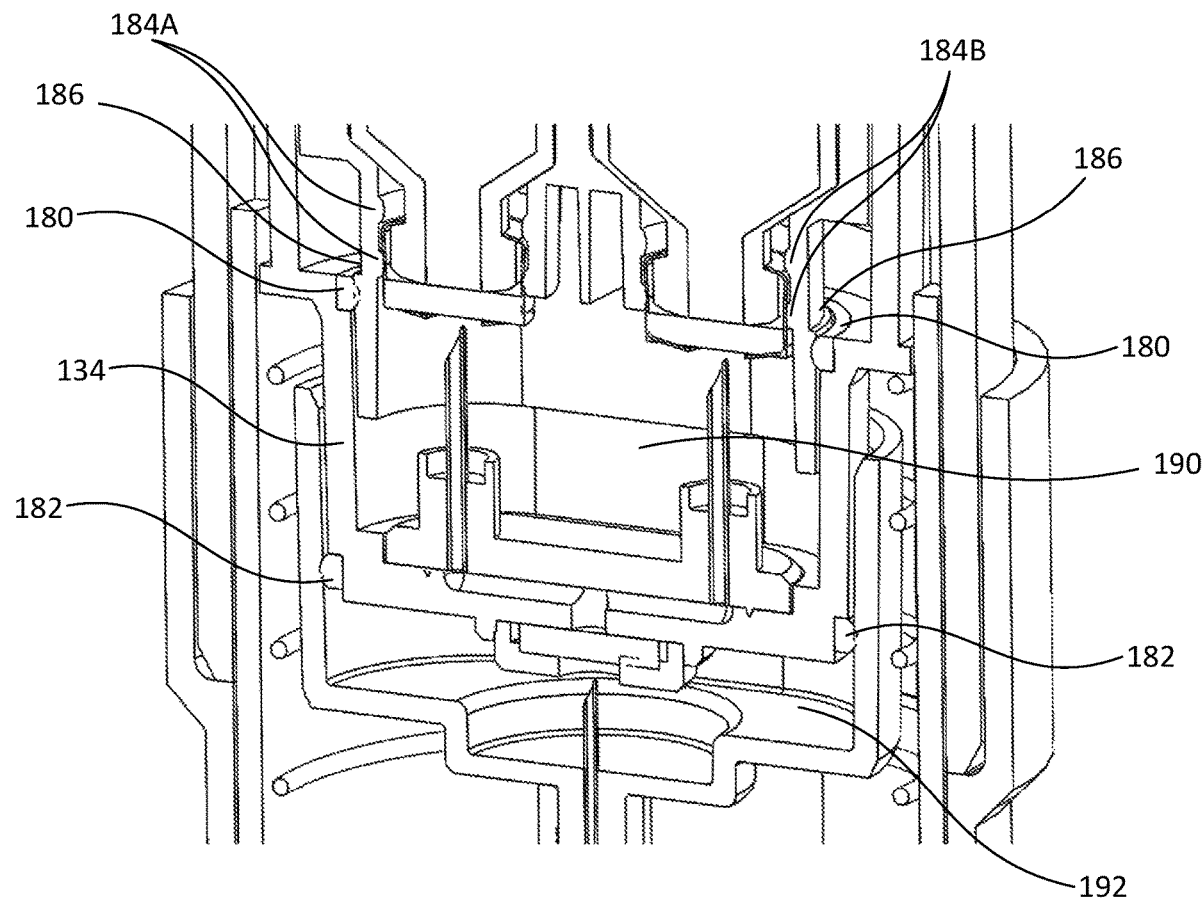
FIGS. 5A-D illustrate various sterility features and their release states associated with the mixing frame for several of the embodiments depicted herein.
Figure 5B:
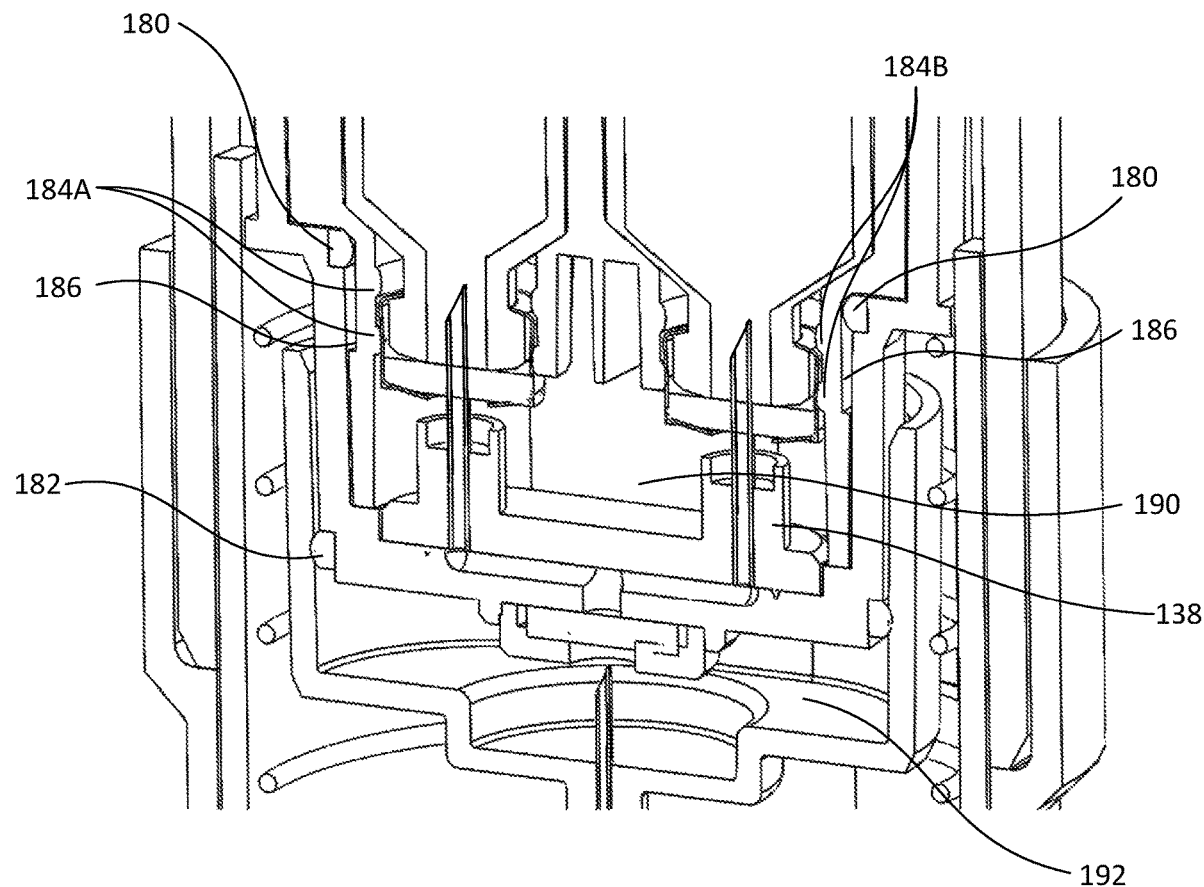

FIGS. 5A-D illustrate various sterility features and their release states associated with the mixing frame 134 for several of the embodiments depicted herein. Although the mixing frame 134 is from the mixing device 100 above, it should be noted that this same mixing frame with associated components and functionality can be likewise configured into other embodiments described later. As shown in FIG. 5A, the mixing frame 134 can include an upper sterility seal 180 and a lower sterility seal 182. upper sterility seal 180 is shown disposed on the inner side of the mixing frame 134, while lower sterility seal 182 is shown disposed on the outer side of the mixing frame. The mixing frame 134 in conjunction with the container holder 132 form a sealed sterility volume 190 about the mixing hub. Upper sterility seal 180 interfaces with the sidewall of the container holder 132 to form a seal. Within the container holder 132 are a plurality of container holder sealing ridges 184A, 184B that interface with the lower portion of the first and second containers 122A, 122B and also form a sealing interface. Together they maintain the sterility volume 190 until mixing needles each pierce into the containers and form a sterile fluid communication. When the first and second containers are compressed into the mixing needles, which are held in place by the mixing needle hub 138, a venting path is formed, as shown in FIG. 5B. This vent is created as a venting ridge 186 that is formed in the lower portion of the container holder 132 as it translates towards the mixing frame 134 and passes by the upper sterility seal 180 to open up or form a vent, whereby a portion of air or gas disposed in the sterile volume 190 can escape. Thus, a sterile interface can be maintained while the mixing device is stored or transported and prior to use.

Figures 5C, 5D:
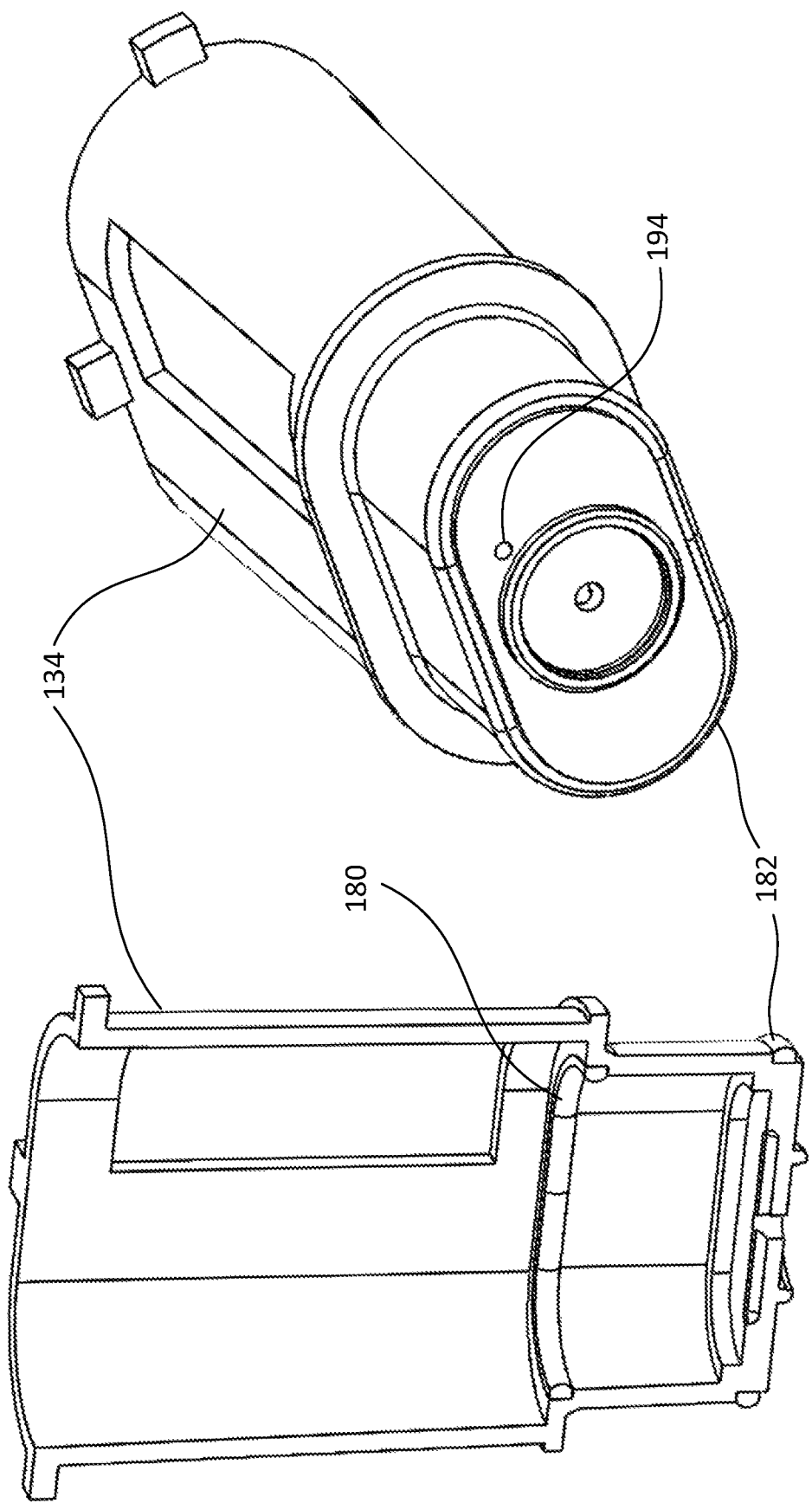

FIGS. 5C-D illustrate a cross-sectional view of the mixing frame 134 (5C) and non-cross-sectional view (5D) of the mixing frame 134 separate from the rest of the mixing device. Here it shown how the upper and lower sterility seals are formed about an entire sealing section of the mixing frame. Of note and to be discussed below is shown an optional venting hole or aperture 194 in a lower portion of the mixing frame 134.

Figure 6A:
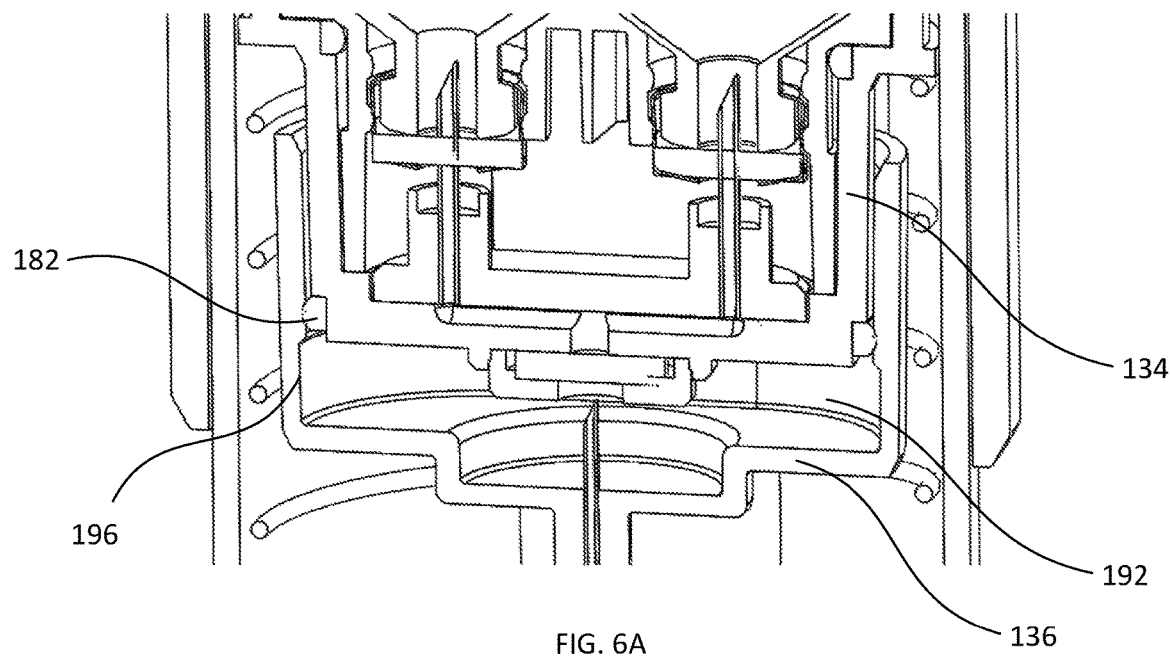
FIGS. 6A-B illustrate various sterility features and their release states associated with the delivery hub and mixing frame 134 depicted herein.
Figure 6B:
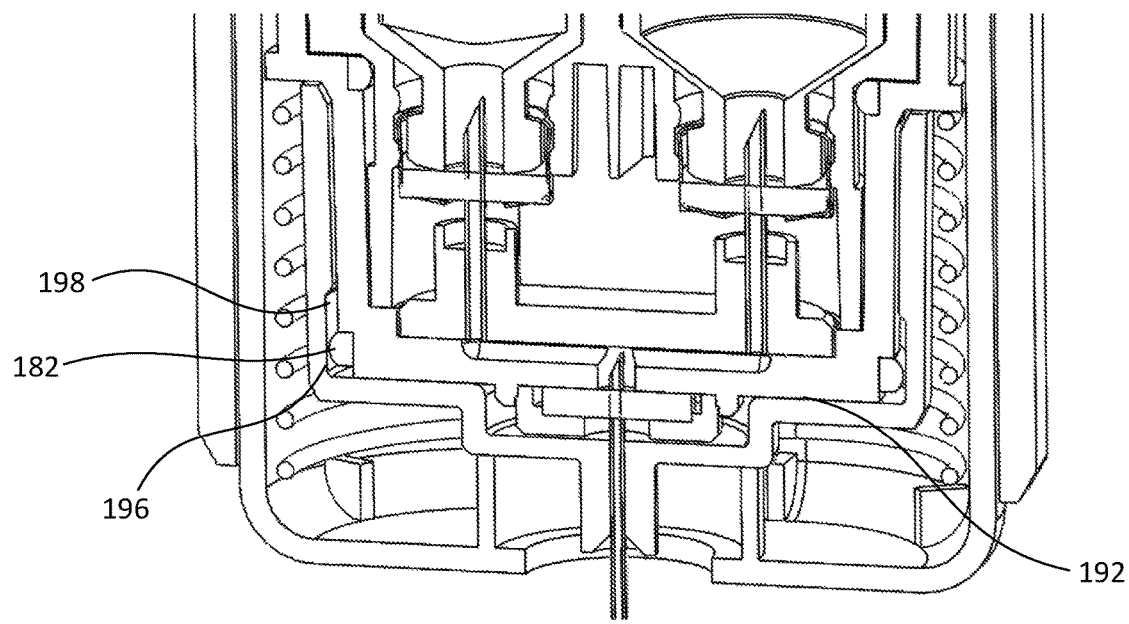

FIGS. 6A-B illustrate various sterility features and their release states associated with the delivery hub 136 and mixing frame 134. A sealed sterility volume 192 associated with the delivery hub 136 is shown in FIG. 6A. This is created by the mixing frame 134 engaging the delivery hub 136, and forming sealing barrier where the lower seal 182 is disposed. Similar to embodiment in FIGS. 5A-B, when the delivery hub 136 is pressed upward into the mixing frame 134, the lower sterility seal 182 is able to vent because of the venting region 198 formed as a result of the venting ridge 196. This venting region 198 is shown in FIG. 6B.

As contemplated in an alternative embodiment, instead of creating the venting ridge 196 in the delivery hub 136 sidewall, the air or gas in the sterility volume 192 could escape through the venting hole or aperture 194 formed in the bottom portion of the mixing frame 134.

FIGS. 7A-C illustrate various states of an alternative mixing and delivery device 200, where the delivery components are manually operated. FIG. 7A illustrates the delivery device 200 in a stored state, FIG. 7B illustrates the delivery device 200 in a delivery-initiated state, and FIG. 7C illustrates the delivery device 200 in a fully delivered state. Similar to the mixing and delivery device 100, 200 includes first and second plunger rods 208A, 208B that can transfer the medicament components from the first container 222A to the second container 222B back-and-forth as many times as necessary, to ready for delivery. This back-and-forth fluid communication is enabled once the drive mechanism housing 204 is depressed to create fluid communication between the first and second containers and the fluidic channel. Also similar to 100, device 200 includes a needle shield 250 covered by a cap 206. When the needle shield is depressed however, it only performs the function of locking out the plunger rod 208A as it causes the delivery collar 212 having a ramped edge 260 and protrusion end 262 to translate the release slide 214 over into the plunger rod detent 264. It does not cause the release of a delivery spring, because there is no delivery spring in this embodiment. When the user is ready to deliver the mixed medicaments, they manually depress the plunger rod 208B. It should also be noted that the mixing initiation phase and piercing of the delivery seal, in addition to the features maintaining sterility volumes above can all be incorporated into 200 similar to that of 100.

Figure 8A:
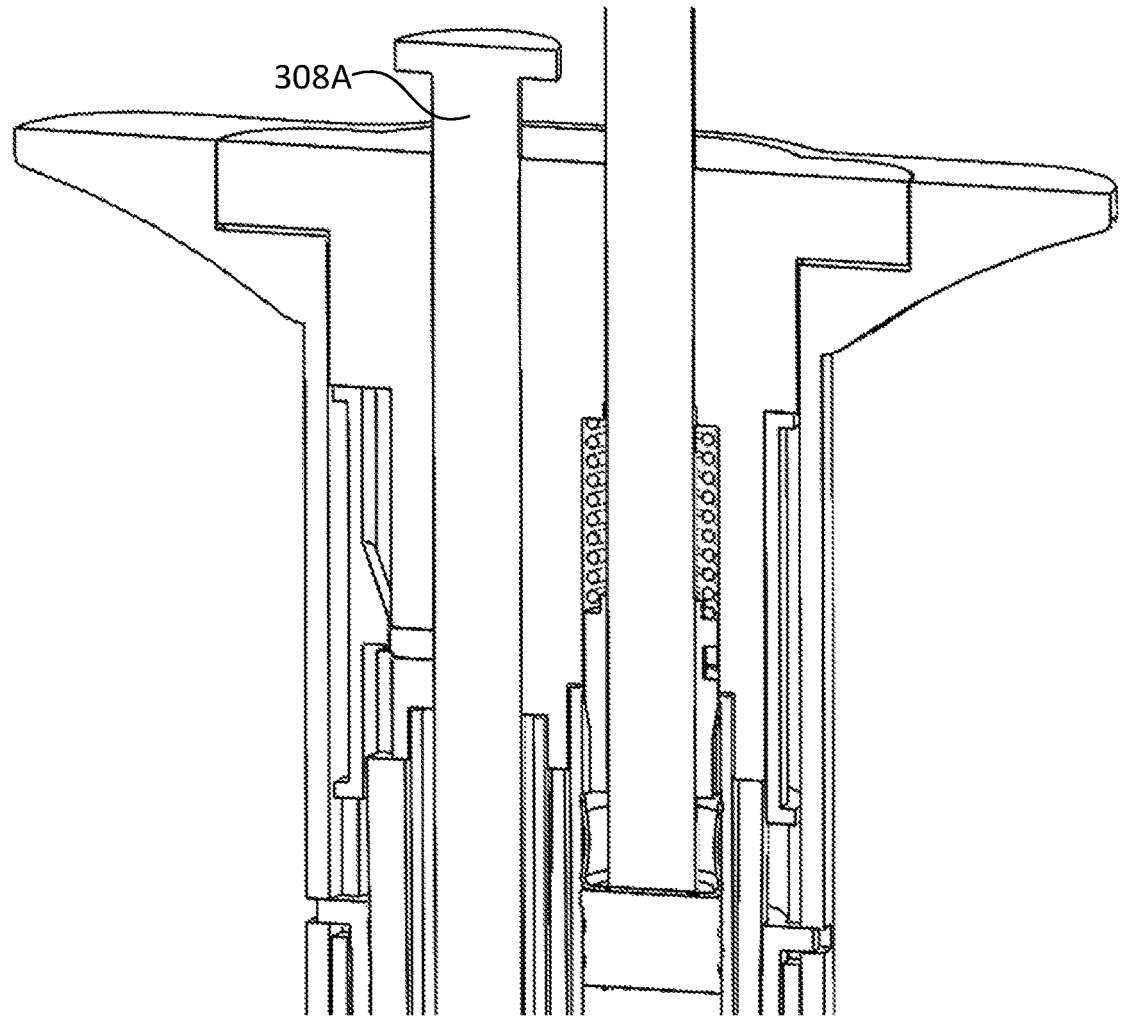

FIGS. 8A-C illustrate another variant of the mixing devices (100, 200) already described, where the plunger rod is devoid of a plunger rod lockout feature. The device 300 illustrates a similar release slider 314 as those described above, except this one does not interface with a plunger rod detent, because none exists in this embodiment. Instead, the release slider can apply a pressure on the side of the plunger rod 308A. The pressure in combination with the pressure of the plunger can be sufficient to prevent additional backflow into the first container once the delivery assembly and specifically the delivery needle establishes fluid communication with the fluidic communication channel. In another embodiment, not shown, the mixing and delivery device doesn't include a release slider at all and relies on the friction of the plunger to prevent back flow into the first container. This friction does not necessarily need to be a lot of friction, just enough to overcome any back pressure of the fluid flow is traveling through and out of the delivery needle. In another embodiment, where neither the frictional forces between the plunger and container, nor the pressure of the release slider on plunger rod 308A is sufficient to prevent backflow, the user themselves can apply pressure in order to maintain direct contact with the plunger rod 308A using a finger, thumb, or other appendage to ensure the position of plunger rod 308A is maintained throughout the duration of the delivery step.

Figure 9A:
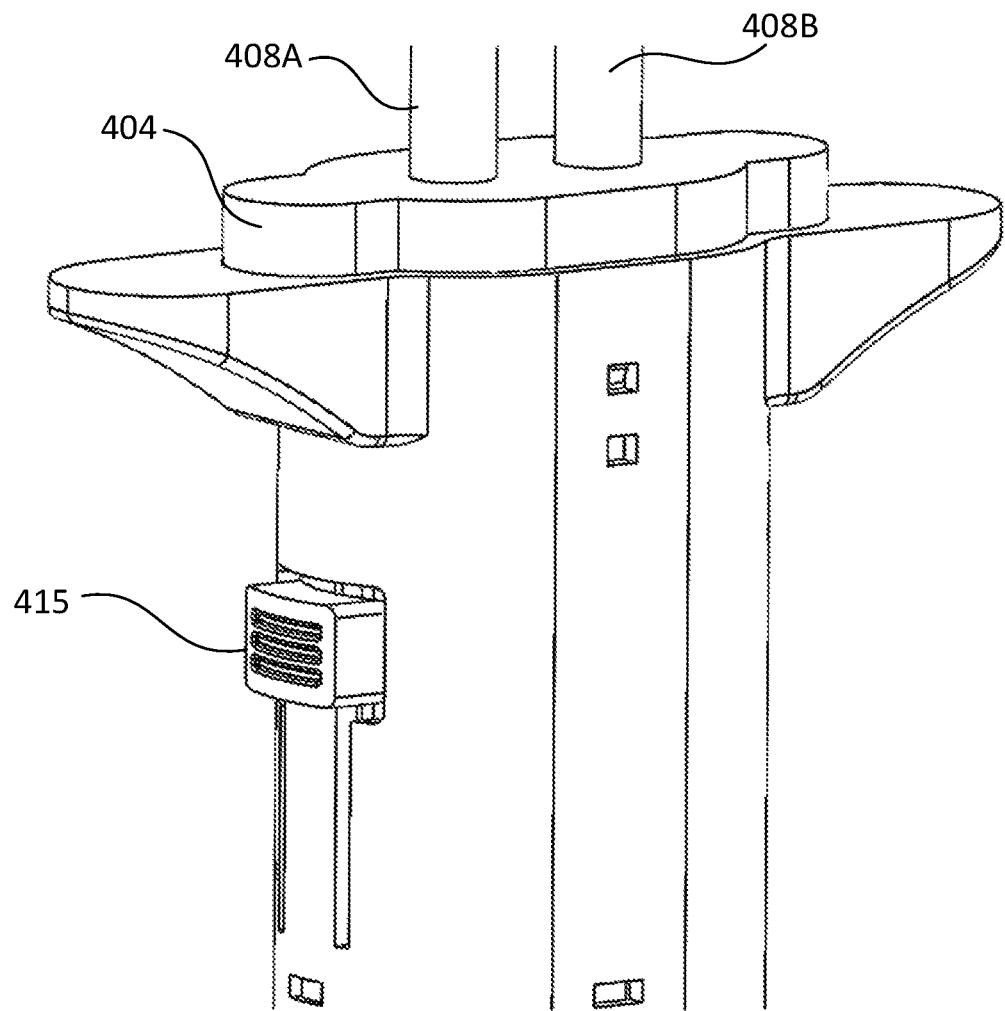
FIGS. 9A-C illustrate yet another variant of the mixing devices already described including a side locking and/or actuation button.
Figure 9B:
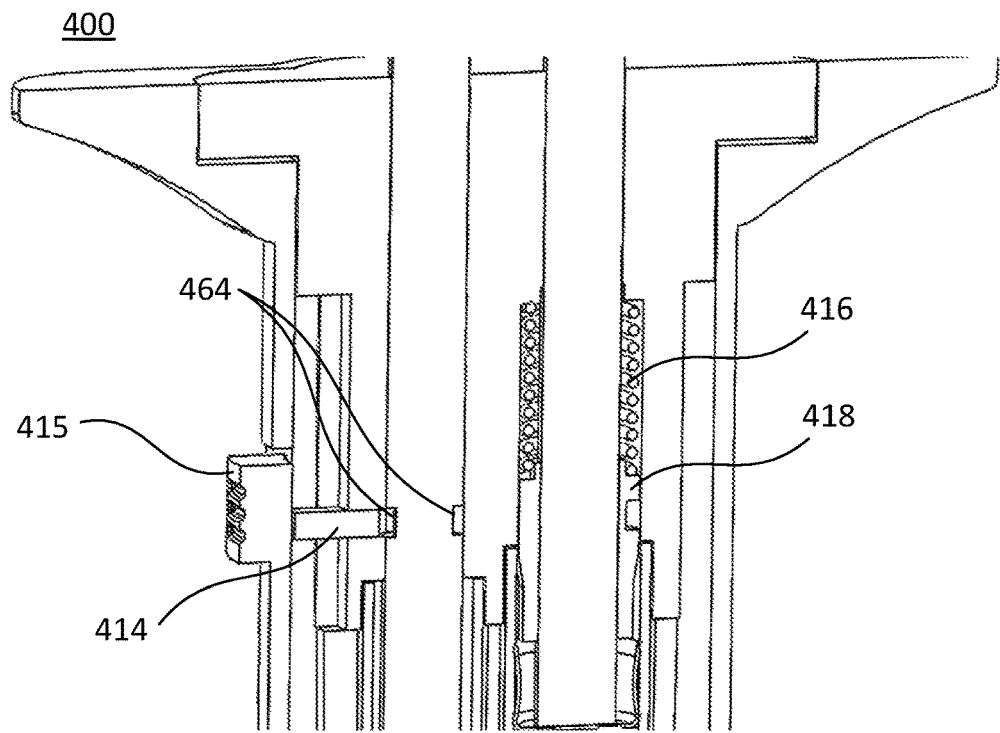
Figure 9C:
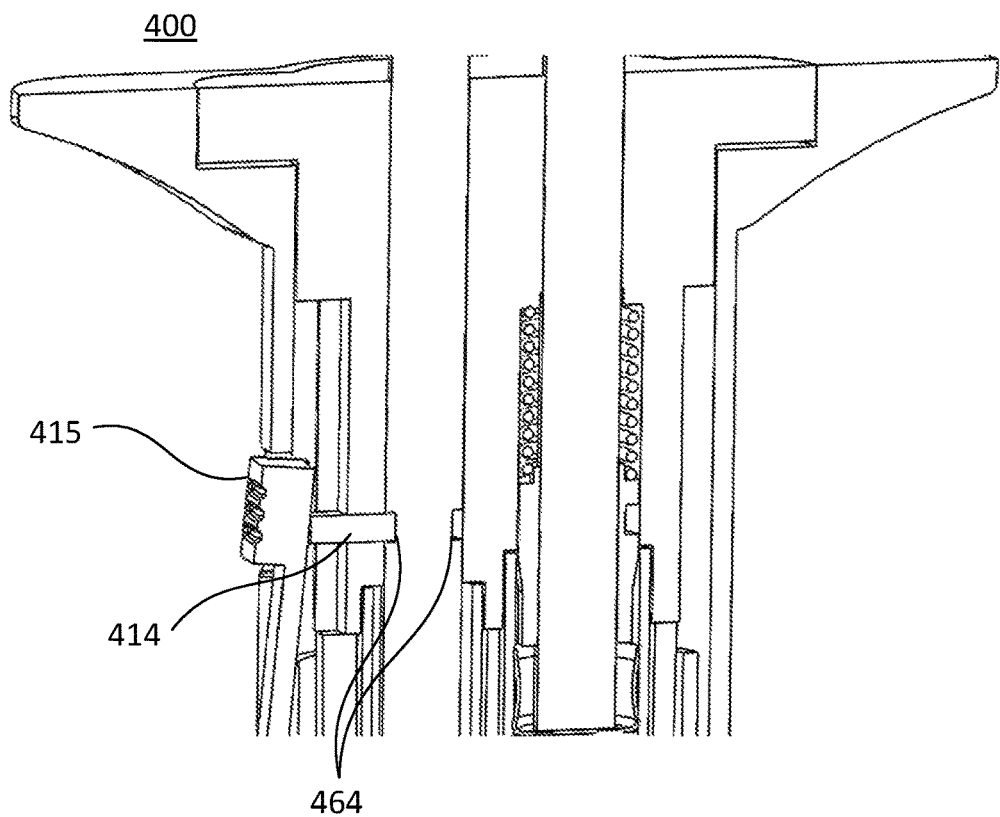

FIGS. 9A-C illustrate yet another variant of the mixing devices 400 already described including a side actuation button 415 that could be incorporated into any of the embodiments described above. Here the function of the side actuation button 415 is at least two-fold. One it causes the release slider 414 to engage with the rod plunger detent 464 and lock into place the plunger rod 408A. Second, it can cause the delivery spring 416 (for embodiments that include a delivery spring) to be released and automatically drive the delivery piston 418 to drive the plunger (and plunger rod 408B) to force the mixed medicament disposed in the corresponding container to be driven out of the container. This embodiment does not require the locking of the plunger rod or triggering of the delivery actuation via the needle shield and can enable a host of alternative delivery embodiments described below and in other figures. Drive mechanism housing 404 functions similar to 104 noted above.

FIGS. 10A-C illustrate different cross-sectional views of the release slider engaging with the plunger rod detent at various states. In FIG. 10A the release slider 114, 414 is positioned in that corresponding to a stored or mixing initiated state, where the travel of the plunger rods 108A, 408A are uninhibited. FIG. 10B illustrates when the plunger rod detent 164, 464 comes into position where the release slider 114, 414 can engage. In both FIGS. 10A and 10B the release slider also holds the delivery piston 118, 418 in shear so the delivery spring 116, 416 cannot be released. In FIG. 10C the release slider is translated over by delivery collar 112 to engage the plunger rod 108A, 408A and fully release the delivery piston 118, 418. It should be noted that the version shown here includes the delivery collar 112 as the mechanism translating the release slider; however, as noted in parenthesis, this could be substituted by the side actuation button 415 previously described and depicted.

Figure 11A:
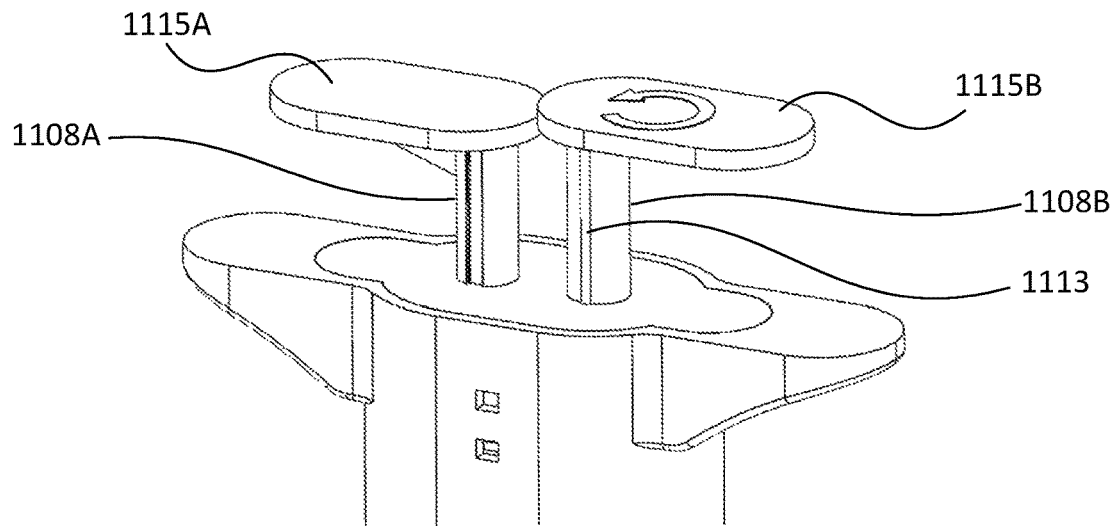
FIGS. 11A-C illustrate an alternative form of first and second plunger rods that including flanges.
Figure 11B:
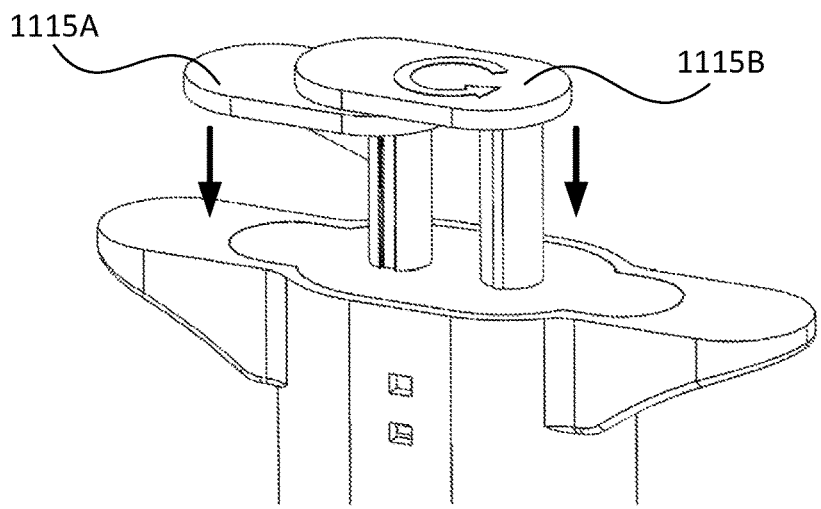
Figure 11C:
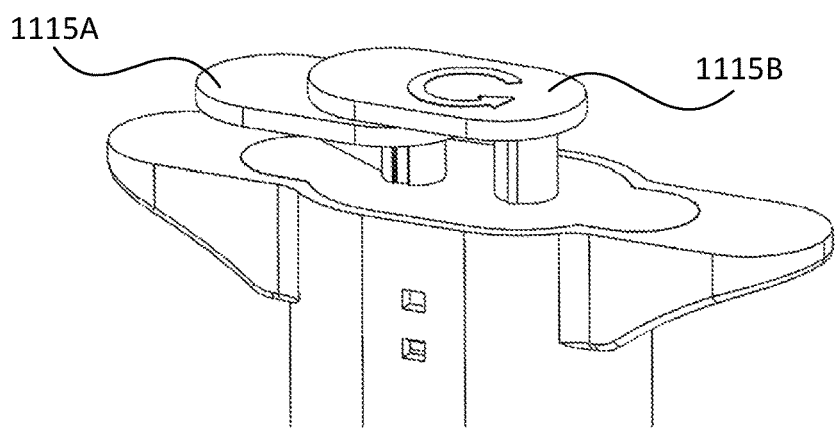

For embodiments where the intent is to depress both plunger rods simultaneously, the solution shown in FIGS. 11A-C illustrate an alternative form of first and second plunger rods 1108A, 1108B that including flanges 1115A, 1115B respectively. As shown in FIG. 11A each plunger rod has its own corresponding flange. 11A-C. Here the user rotates 1108B and flange 1115B over until 1115B is over flange 1115A. Now the user can depress flange 1115B, which drives both plunger rods 1108A and 1108B to be able to dispense medicament stored in the respective containers or cartridges that each rod is associated with. In some variations, bump snaps 1113 can be provided on one or both plunger rods, which can assist with locking the plunger rod into place upon rotating the flange. Prior to rotating, the flanges are free from each other and can assist with the pumping of the plunger rods to transfer the medicament between containers until it is in a state ready for delivery, upon which the flanges can be rotated over and depressed together as noted.

Figure 11D:
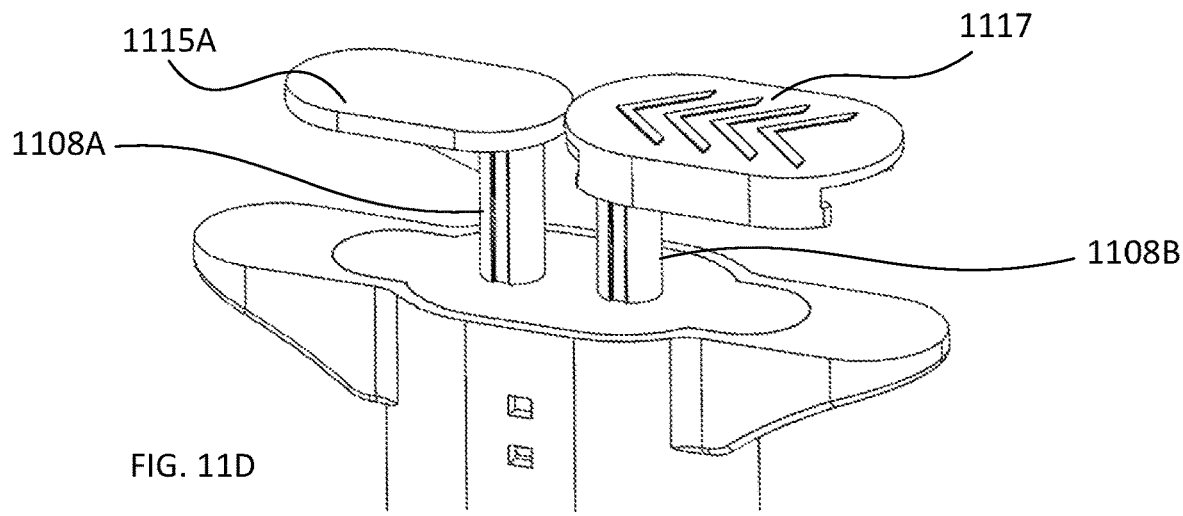
FIGS. 11D-F illustrate an alternative form of 11A-C to simultaneously drive the first and second plunger rods.
Figure 11E:
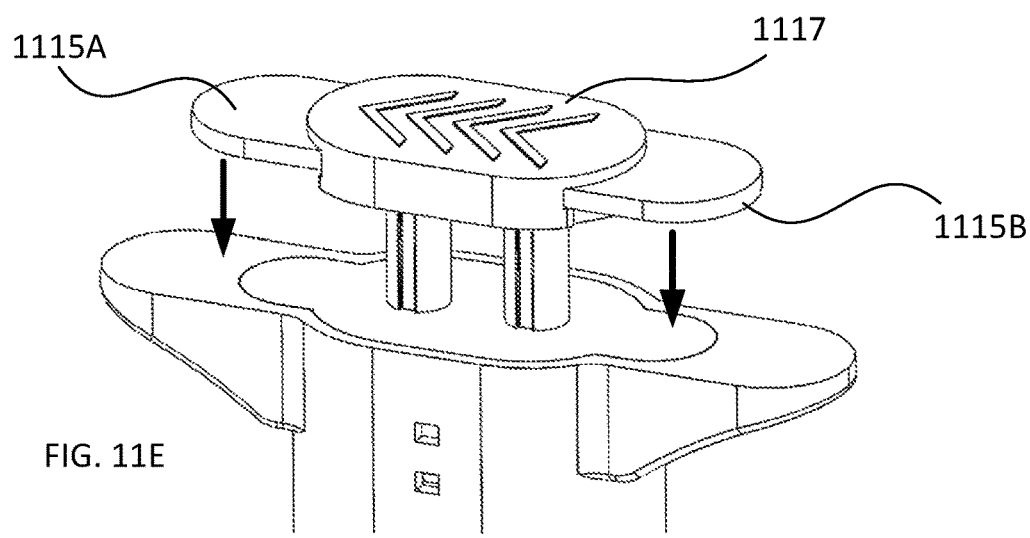
Figure 11F:
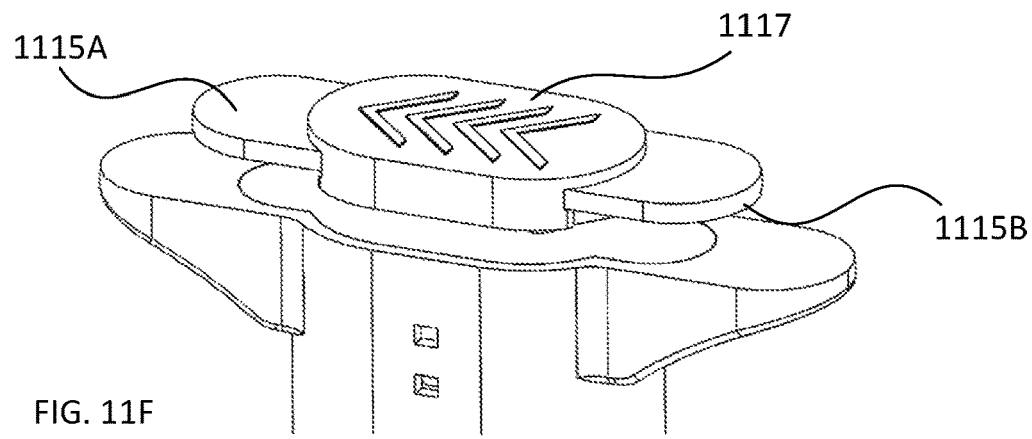

FIGS. 11D-F illustrate an alternative form of the solution of FIGS. 11A-C to simultaneously drive the first and second plunger rods. Instead of rotating flange 1115B over flange 1115A, flange 1115B can including a sliding lock mechanism 1117 that when the device is in a ready state for delivery the mixed medicaments, 1117 can slide over part of 1115A, and lock 1115A relative to 1115B, such that when either side is depressed it drives both plunger rods 1108A and 1108B simultaneously. It should be noted that these two examples are exemplary and not limiting.

Figure 12:
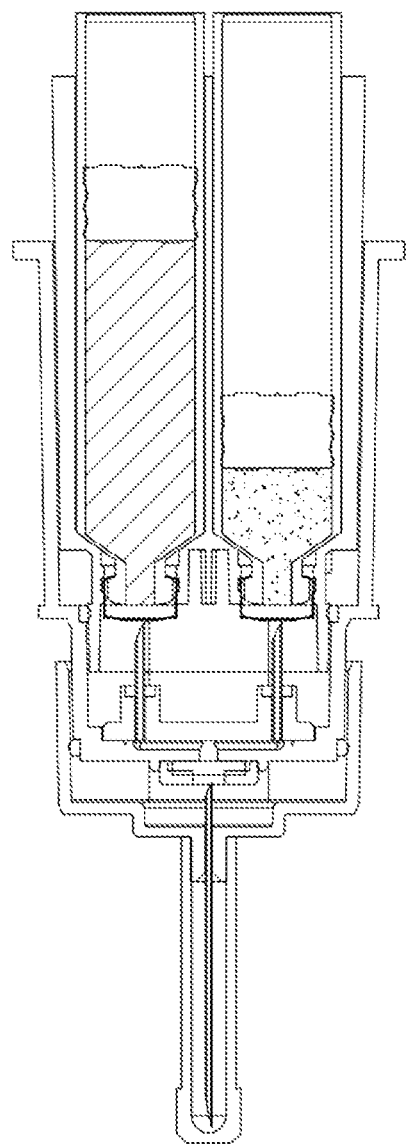
FIG. 12 illustrates an embodiment where the first and second containers are the same size.

FIG. 12 illustrates an embodiment where the first and second containers are the same size, in contrast the embodiments previously shown and described where the first and second containers are of different sizes and volumes.

FIGS. 13A-C illustrate a delivery attachment device including a fluidic channel disposed therein. FIG. 13A illustrates a dual chamber primary drug container assembly. FIG. 13B illustrates an exploded view of the device of FIG. 13A, which includes a cartridge frame, pre-filled cartridges and a needle assembly and sterility barrier. The needle assembly shown in FIG. 13C includes a fluidic channel to transfer medicament back and forth between the two cartridges or containers similar to the above embodiments. Here the needle is embedded in the sterility barrier that covers the needle to prevent the fluid from escaping the needle tip until the medicament components stored therein are completely mixed and ready for delivery.

Figure 13E:
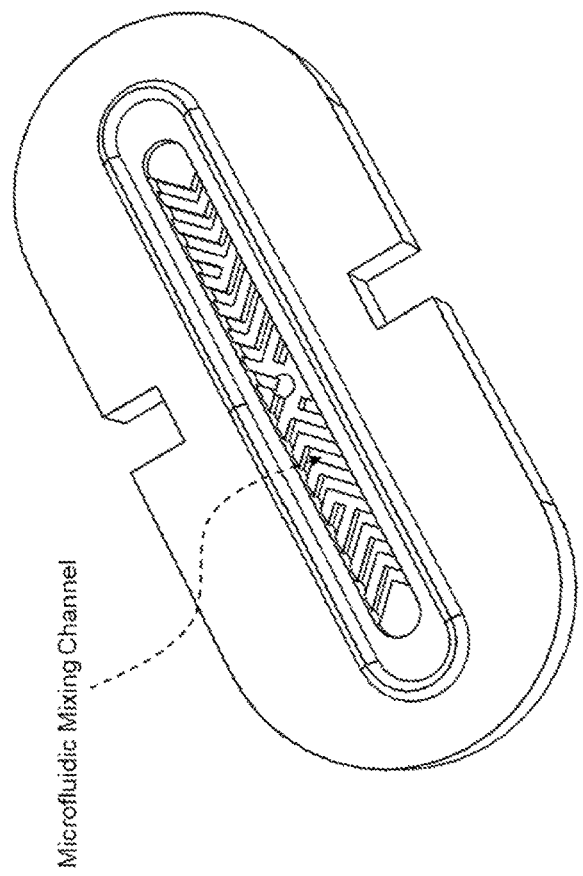
FIGS. 13D-E illustrate the delivery attachment device including fluidic mixing features.
Figure 13D:
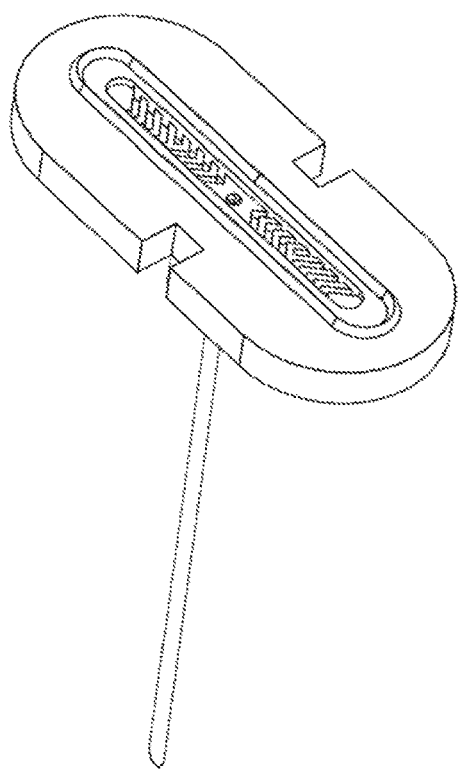

FIGS. 13D-E illustrate the delivery attachment device including a channel with fluidic mixing features disposed therein. These fluidic mixing features can aid in medicament component mixing process as they are translated fluidly back and forth between each cartridge or container.

Figure 14:
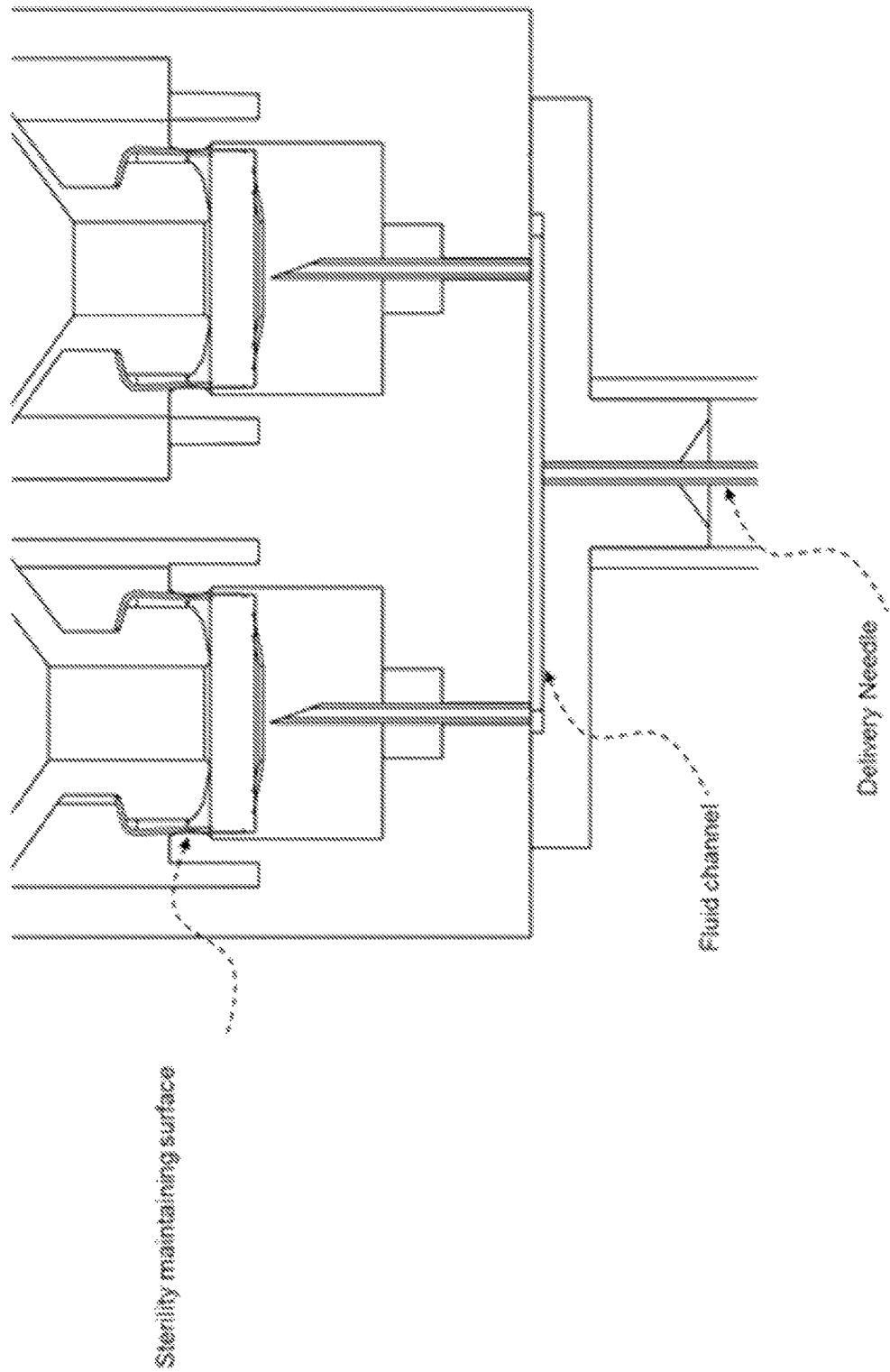
FIG. 14 illustrates another embodiment where the delivery needle is fully integrated with the fluid channel.

FIG. 14 illustrates another example where the delivery needle is fully integrated into the fluid channel prior to and throughout the mixing process. Similarly, to FIG. 13A the distal end of the needle would be embedded in a sterility barrier that covers the needle to restrict flow down the delivery needle until the medicament components are fully mixed and ready for delivery.

FIGS. 15A-D (external views) and FIGS. 16A-D (cross-sectional views) illustrate another embodiment that includes a single manual plunger rod with a return transfer mechanism. Mixing device 500 can include (or not include) the various delivery assemblies noted above. The primary purpose of this device is to illustrate a single plunger rod transfer mechanism. In the stored state, mixing device 500 includes a housing 502 that includes a mixing or drive mechanism housing 504, similar to other embodiments that when depressed, fluidly connects the first and second container disposed therein and places them in a position to transfer medicament components back and forth between the containers, thus causing the medicaments components to mix.

Figure 15B:
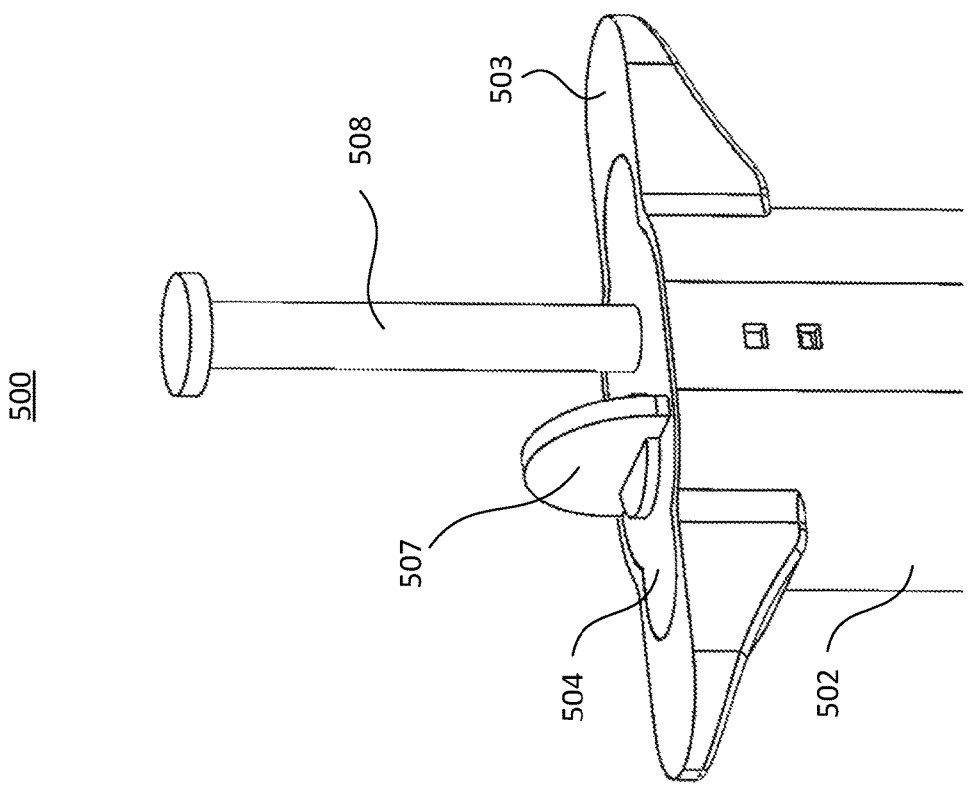
Figure 15A:
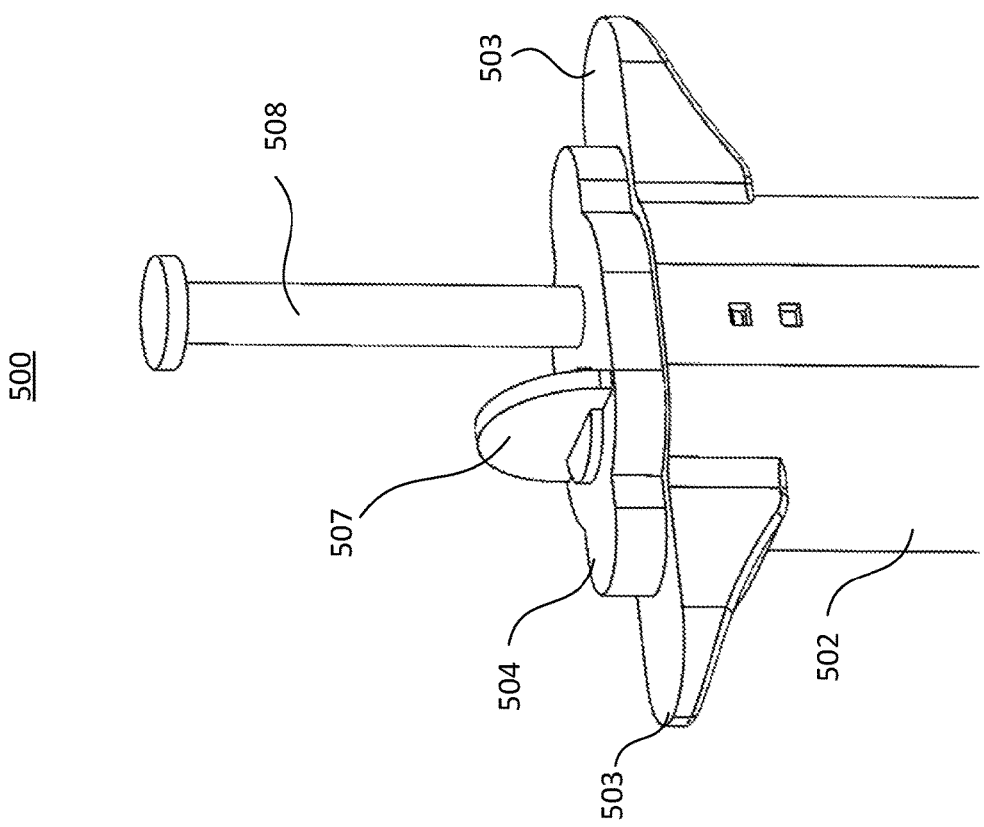
Figure 16B:
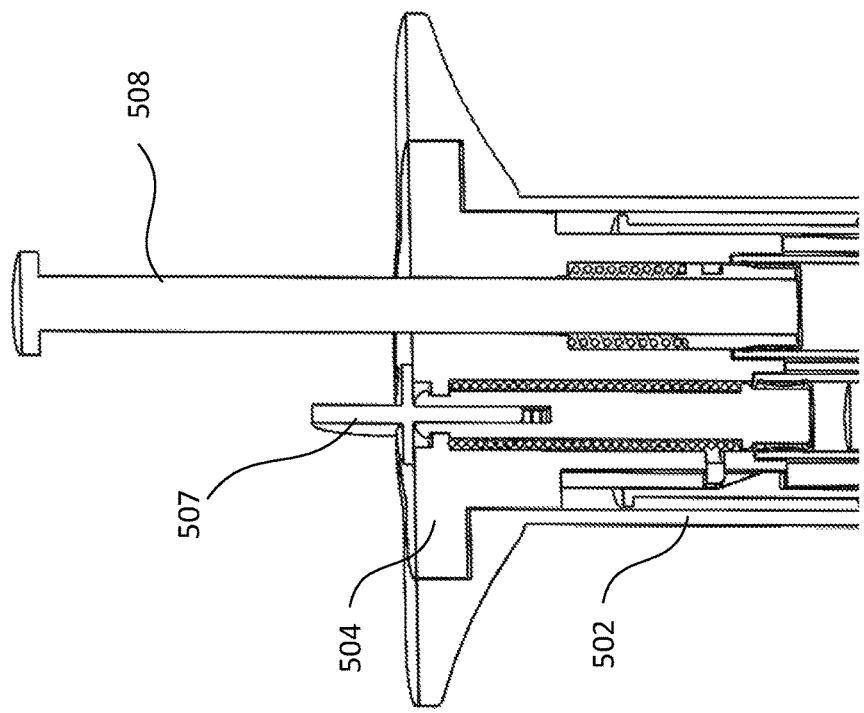
Figure 16A:
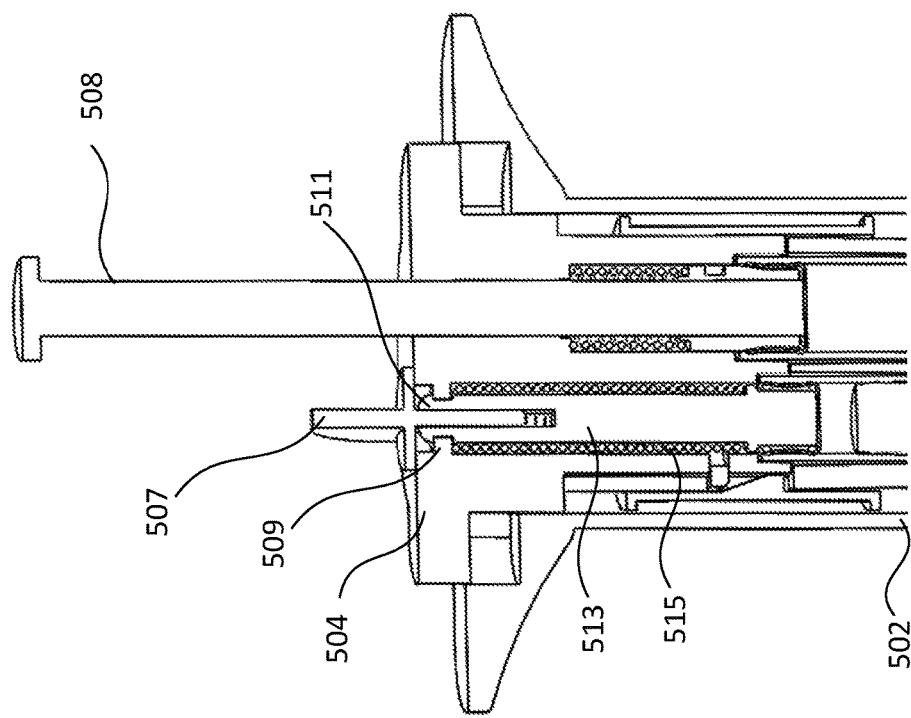

Similar to the above embodiments, device 500 includes a pair of side flanges 503, though not explicitly called out above, to aid a user to grip and pump or depress the plunger rod 508 with using their hand. FIGS. 15A/16A showed device 500 in the stored state. FIGS. 15B/16B showed device 500 in the mixing initiation state, where the medicament components are ready to be mixed.

Device 500 includes a safety pin 507, that upon releasing (pulling out) allows a transfer spring 515 to release energy and force a driver 513 downward or in a distal direction to act on a plunger and force a medicament component from the first container into the second container associated with plunger rod 508. The driver includes a pair of driver arms 511 that interface with a release edge 509, When the arms are forced apart by the safety release 507 the arms cannot disengage from the ledge 509; however, once the safety release 507 is removed the arms are free to disengage from the ledge 509. This disengagement is shown in FIGS. 15C/16C.

Now that the medicament component has transferred from the first container to the second container, the user can depress plunger rod 508 to return the medicament components from the second container back to the first container. In the process, the user recompresses and/or reenergizes the transfer spring 515, and upon releasing the plunger rod 508, causes the mixed medicament components to automatically transfer back to the second container. In this embodiment, the user only needs to depress the plunger rod once and the result is the medicament components transfer back and forth with each depression and release. Once the medicament components are mixed and ready, the user can appropriate deliver the mixed medicament components, using one of the delivery assemblies or systems discussed above and depicted in the earlier drawings. This can either be achieved through manual administration, or triggering via the needle shield to provide for delivery via a pre-stored energy source.

Figures 17C, 17D:
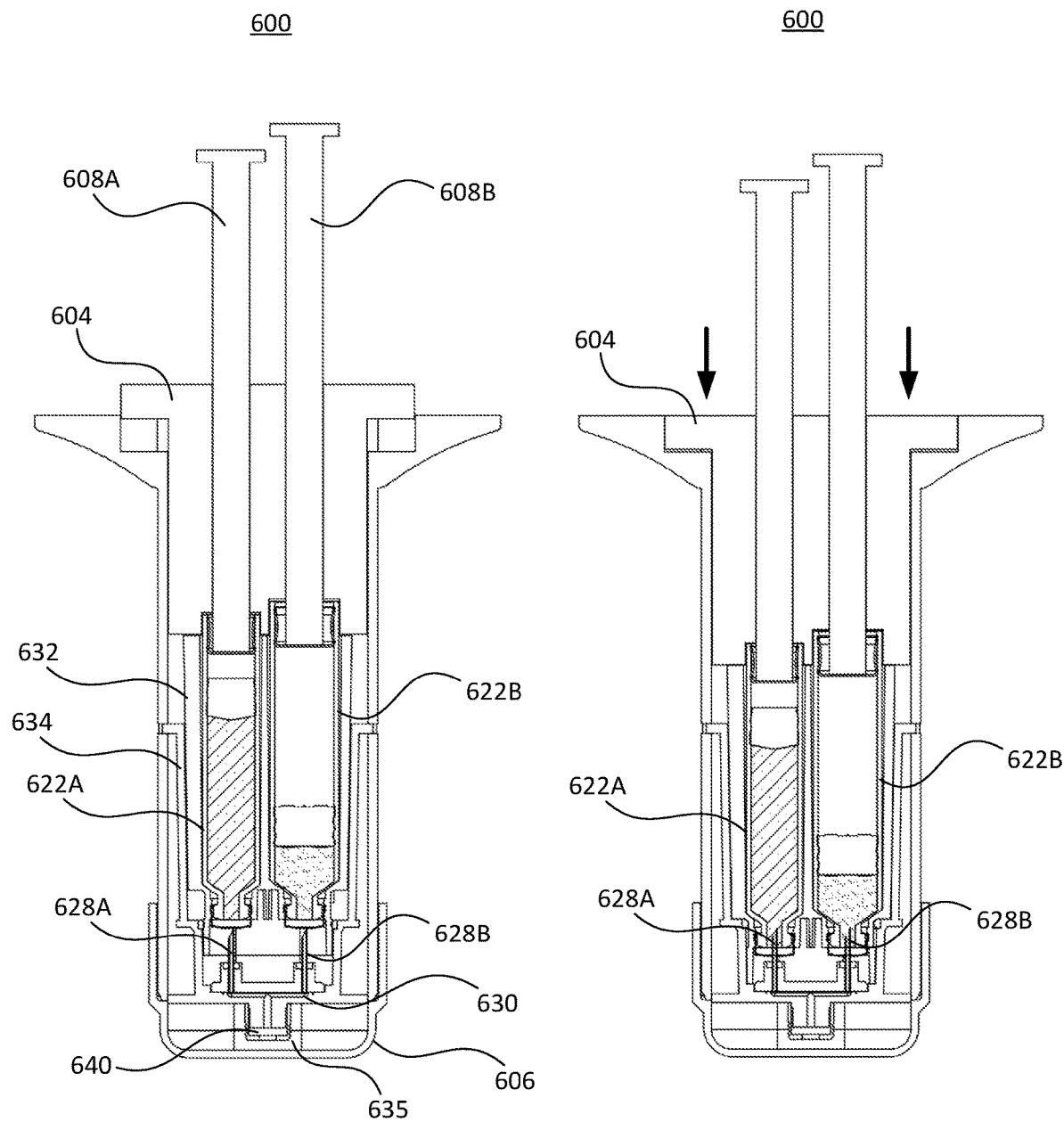
Figure 17G:
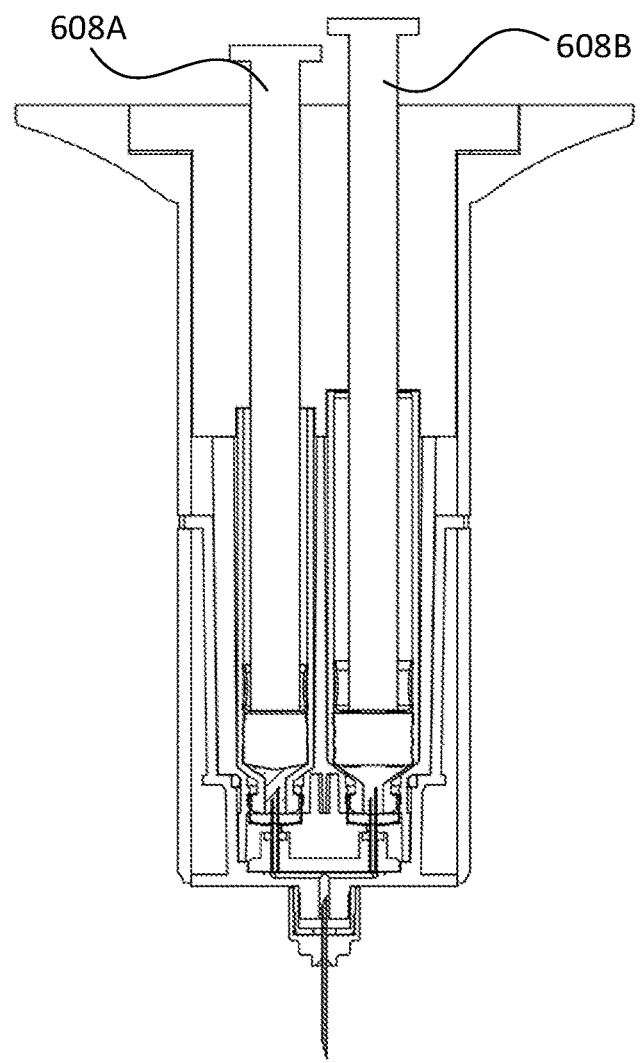

FIGS. 17A-G illustrate various states of a device 600 that includes an attachable delivery mechanism 645. As illustrated in FIGS. 17A-B the attachable delivery mechanism 645 can be screwed on to the delivery connection 635 of the mixing device 600. FIGS. 17C-G illustrate further the various states of mixing and delivery similar to embodiments described above. Here device 600 includes a housing 602, plunger rods 608A and 608B are configured to interface with plungers disposed in containers 622A and 622B respectively. Each container configured to hold a medicament component. When the drive mechanism housing 604 is depressed, it causes the container holder 632 disposed within the housing to move distally into the mixing frame 634. As it travels distally, each container 622A and 622B are driven into respective mixing needles 628A and 628B, which are in fluid communication with the fluidic channel 630. Once each container is in fluidic communication with the other chamber, the plunger rods can be alternately depressed to drive medicament components from one container and back one or more containers until the mixed medicament components are ready to be delivered. Once in the ready state, as shown in FIG. 17F the delivery assembly 645 can be connected to the delivery connection 635 once the cap 606 is removed. The delivery assembly is comprised of a delivery needle 644, which has a piercing end 648 and a delivery end 646. The piercing end 648 is configured to pierce through the delivery seal 640 and become in fluid communication with the fluid channel 630. At this stage each of the plunger rods can be depressed to delivery or otherwise transfer the mixed medicament components. Once again, this embodiment 600 can have features that are integrated from above and would be well within the scope of this description. For example, device 600 does not include an automated delivery feature or automated transfer mechanism, such as some of the embodiments above include, which could be integrated herein as a variant to this embodiment.

Figure 18A:
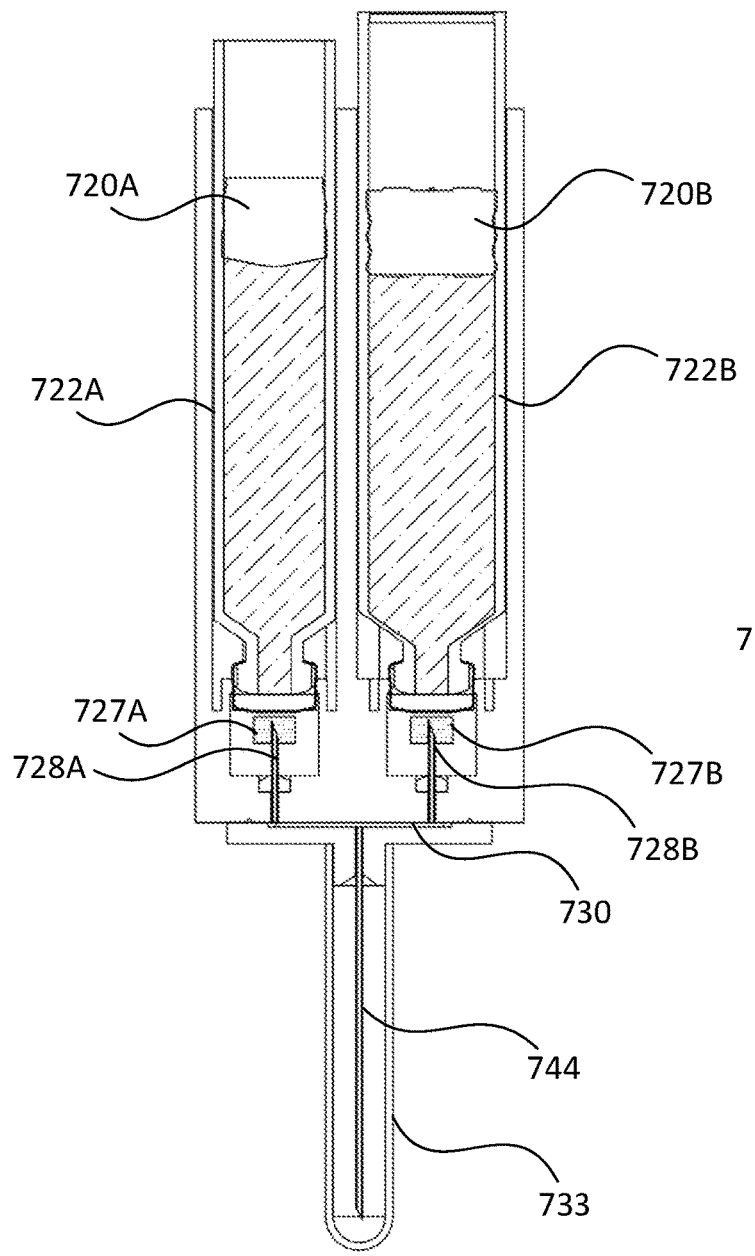
FIGS. 18A-E illustrate an alternative sterility system for the mixing needles and fluidic channel of a delivery device having multiple containers.

FIGS. 18A-E illustrate various states of an alternative system for the mixing needles and fluidic channel of a delivery device 700 whereby mixing is not intended but the medicaments from both containers are dispelled independently from each other. FIG. 18A illustrates a stowed state for device 700, here a first container 722A includes a first medicament, a first plunger 720A forming the backstop of the first medicament, a first container seal 726A, a first sterility seal 727A that has a first piercing needle 728A partially disposed therein that is connected to fluidic channel 730, which is in fluid communication with delivery needle 744, where the delivery needle 744 is partially embedded in a sterility barrier 733. Similarly, a second container 722B includes a second medicament, a second plunger 720B forming the backstop of the second medicament, a second container seal 726B, a second sterility seal 727B that has a second piercing needle 728B partially disposed therein that is connected to fluidic channel 730.

Figure 18B:
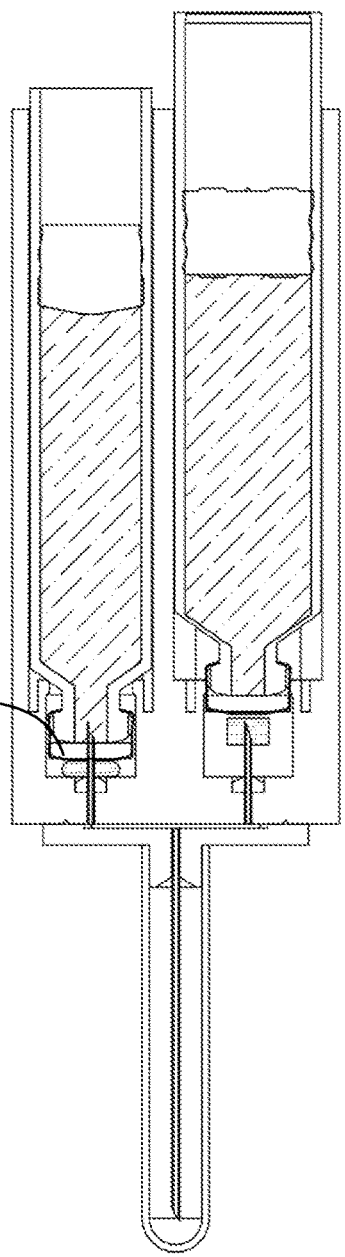
Figure 18C:
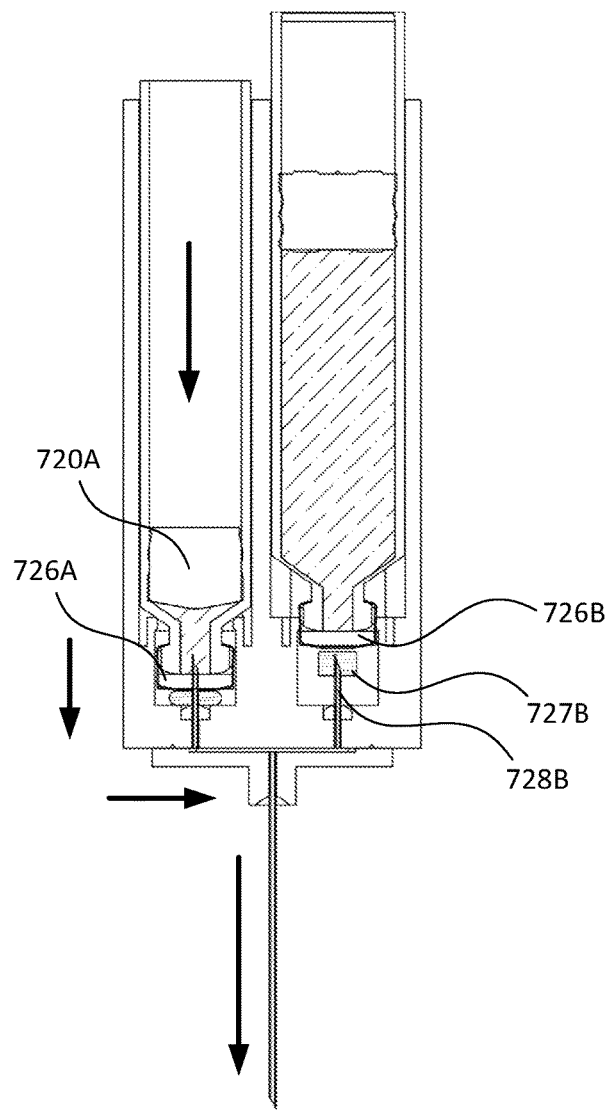
Figure 18D:
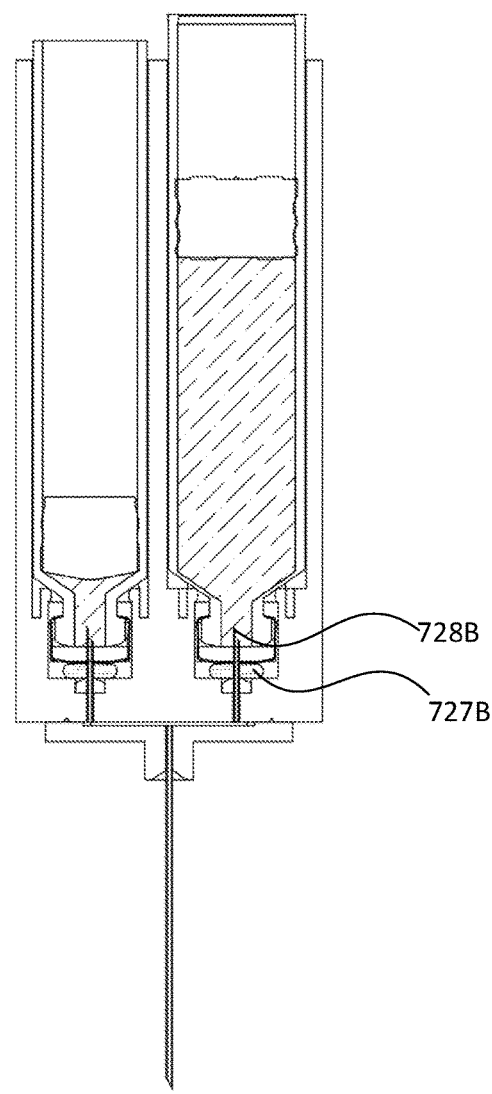

As shown in FIG. 18B, when the first container 722A is pressed into the sterility seal 727A the first piercing needle 728A extends upwards into and through the first container seal 726A to create fluid communication with the first medicament component stored therein. The plunger 720A can then be depressed to deliver the first medicament component out through the delivery needle 744. During this first delivery the second container 722B remains sealed from the fluidic channel, until, as shown in FIG. 18D, the second container is similarly pressed into the piercing needle 728B and causes the second sterility seal and the second container seal to be fully pierced enabling fluid communication between the second container 722B and the fluidic channel 730.

Figure 18E:
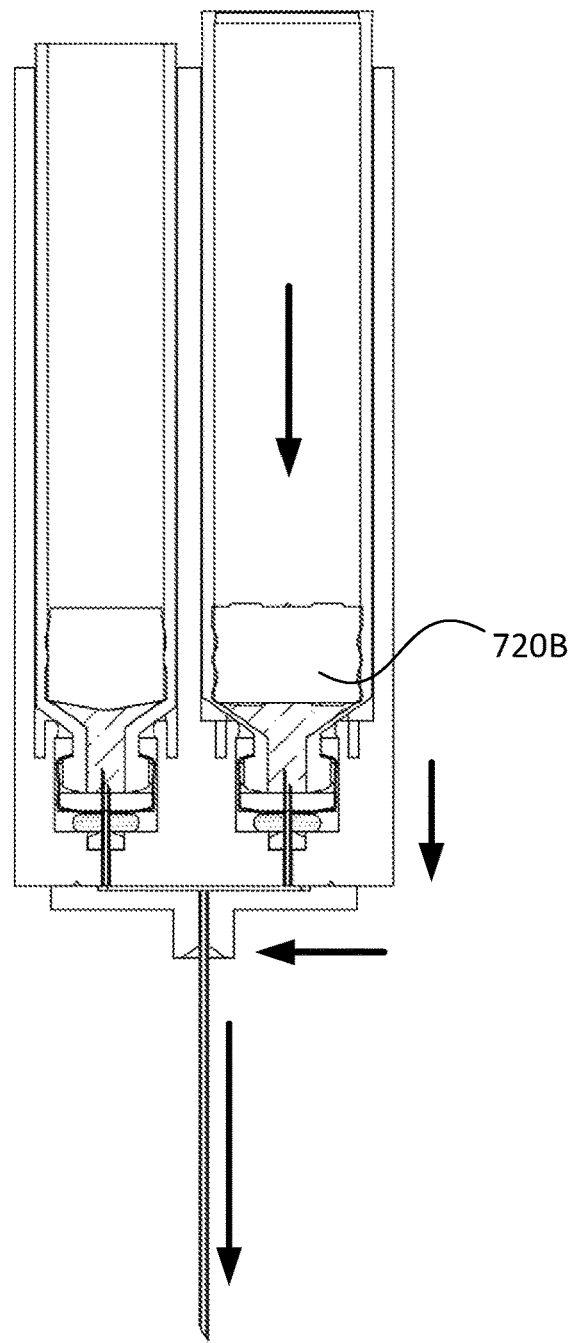

FIG. 18E illustrates the second medicament being delivered out the delivery needle 744 upon depressing the second plunger 720B. Thus, a first medicament component can be held in a sterile situation until delivery as well as the second medicament component. Although these were delivered sequentially, this same device 700 can be configured to deliver simultaneously and also integrated to transfer fluid back and forth between the containers, so long as the sterility barrier 733 is not removed.

Figures 19A, 19B:
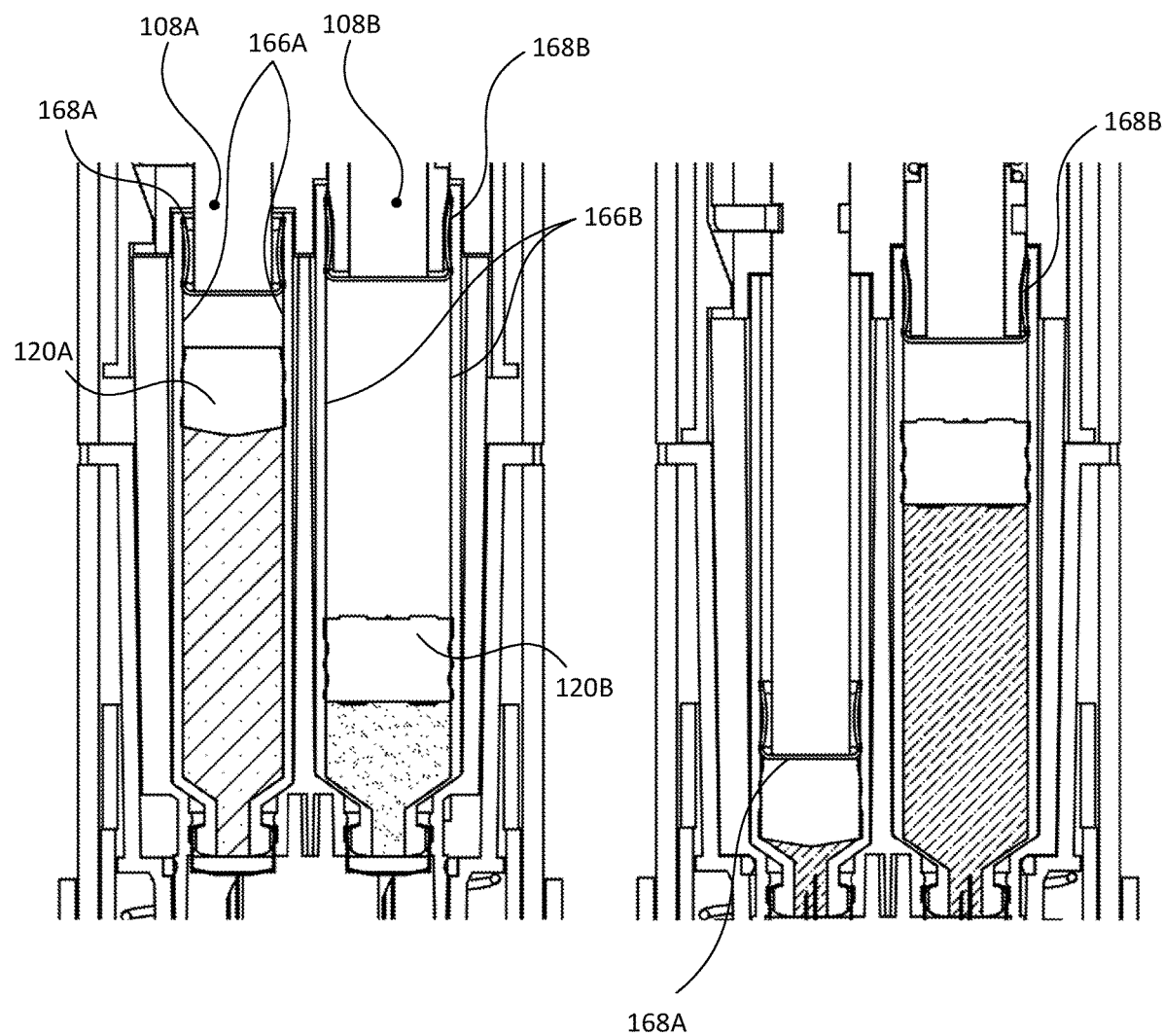
FIGS. 19A-B illustrate sterility caps that can be integrated into any of the devices described herein.

FIGS. 19A-B illustrate the sterility caps 168A and 168B that can be integrated into any of the devices described herein. FIGS. 19A and 19B are enlarged versions of FIGS. 1C and 1E. Disposed between the plunger rods 108A and 108B and the plungers 120A and 120B are sterility caps 168A and 168B. The function of these sterility caps is to provide a sterile inner surface to the inner sidewalls 166A and 166B while in the stored state. Once packaged, the sterility caps prevent debris or any other potential non-sterile contaminates into each of the first and second containers. The sterility caps are formed such that the lower portion forms the sealing barrier, while the sides create a spring-like force to keep the sterility caps in place until moved by the plunger rods. In certain instances, any pockets of air disposed in the upper or proximal portion of the containers can be burped or outgassed through the sidewalls of the sterility caps when the internal pressure reaches a determined threshold that is greater than the spring force. This might arise when initially transferring medicament from one container to the other.

It should be clear from the description above, but to be explicit, it should be readily understood as a result of the various embodiments disclosed that medicament can be delivered from one container first and then from a second container subsequently, as a result of the transferring all of the medicament components to the first or second container, then those mixed medicaments can be delivered from the container where the mixed medicament resides in, the containers can be dispensed simultaneously or subsequently in any order, and the medicament components can also be delivered as a mixed version or each can be delivered subsequently or simultaneously without prior mixing.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

The invention claimed is:

1. A mixing and drug delivery system comprising:
a housing configured to hold a first container and a second container, where in the first container contains a first medicament component and the second container contains a second medicament component;
a first seal;
a second seal;
a seal opening component configured to open, remove or otherwise pierce the first seal and the second seal;
a fluidic channel that allows for fluidic communication between the first and second containers once the seal opening component has caused each of the first and second seals to be altered from a sealed stated to an open state;
a first plunger at least partially disposed within the first container and a second plunger at least partially disposed within the second container,
wherein depressing the first plunger drives a portion of the first medicament from the first container through the fluidic channel into the second container to mix with the second medicament, and
wherein the second plunger when depressed during a second transfer state causes a portion of the mixed medicament in the second container to transfer from the second container through the fluidic channel into the first container;
a delivery assembly, and
an actuation device that includes a stored energy source, whereupon actuating the actuation device causes the stored energy source to release and cause the second plunger to depress and force the mixed medicament disposed in the second container to flow out of the delivery assembly.

2. The drug mixing system of claim 1, further including a delivery assembly having a delivery seal opening component and a delivery component, wherein the delivery seal opening component is configured to cause a delivery seal to alter from a sealed state to an open state, thus allowing the delivery assembly to receive the mixed medicament.

3. The mixing and drug delivery system of claim 1, wherein the actuation device is further coupled to a locking mechanism and upon actuating of the actuation device, the actuation device causes the locking mechanism to engage with the first plunger, thus preventing the first plunger from moving inwardly or outwardly with respect to the housing.

4. The mixing and drug delivery system of claim 1, further including a needle shield assembly that is coupled to the actuation device.

5. The mixing and drug delivery system of claim 4, wherein the needle shield assembly functions as a bump trigger to actuate the actuation device.

6. The mixing and drug delivery system of claim 5, wherein the actuation device causes a locking mechanism to lock the first plunger in place and prevent it from moving inwardly or outwardly.

7. The mixing and drug delivery system of claim 5, wherein the actuation device is configured to release a stored energy source associated with the second plunger and configured to drive the second plunger.

8. The mixing and drug delivery system of claim 5, wherein depressing the needle shield assembly causes the delivery assembly to cause the delivery seal to alter from a sealed state to an open state.

9. The mixing and drug delivery system of claim 1, wherein the first container and the second container are aligned side-by-side to each other with both distal ends pointing in the same direction.

10. The mixing and drug delivery system of claim 1, wherein the first medicament is in a liquid form.

11. The mixing and drug delivery system of claim 1, wherein the second medicament is in a liquid or dry form.

12. The mixing and drug delivery system of claim 1, further including a safety release disposed about the proximal end of the first container.

13. The mixing and drug delivery system of claim 12, further including a transfer spring and a driver, wherein the driver is configured to engage with the first plunger.

14. The mixing and drug delivery system of claim 13, whereupon removal of the safety release causes the driver to depress the first plunger.

15. The mixing and drug delivery system of claim 14, further including a plunger rod associated with the second plunger, and whereupon depressing the plunger rod causes a portion of mixed medicament to transfer to the first container and recompress the transfer spring.

16. The mixing and drug delivery system of claim 15, whereupon releasing the depressed plunger rod causes the recompressed transfer spring to release energy causing the driver to automatically depress the first plunger and transferring a portion of the mixed medicament back into the second container.

17. The mixing and drug delivery system of claim 1, wherein the seal opening component is comprised of at least one mixing needle.

18. The mixing and drug delivery system of claim 17, wherein the at least one mixing needle is fluid connection with the fluidic channel.

19. The mixing and drug delivery system of claim 17, wherein the mixing needle is supported by a mixing needle hub.

20. The mixing and drug delivery system of claim 1, wherein the seal opening component is affected by a fluid communicating mechanism extending from the housing, wherein the fluid communicating mechanism is configured to be depressed into the housing.

21. The drug mixing and drug delivery system of claim 1, wherein the first container, second container, first plunger, second plunger and fluidic channel are configured to transfer a portion of the mixed medicament back and forth into each of the first and second containers multiple times through a plurality of transfer states.

* * * * *